US010682436B2

(12) United States Patent
Freyman et al.

(10) Patent No.: US 10,682,436 B2
(45) Date of Patent: Jun. 16, 2020

(54) IN-SITU FORMING FOAM FOR THE TREATMENT OF VASCULAR DISSECTIONS

(71) Applicants: Toby Freyman, Lexington, MA (US); Meghan McGill, Northborough, MA (US)

(72) Inventors: Toby Freyman, Lexington, MA (US); Meghan McGill, Northborough, MA (US)

(73) Assignee: Arsenal Medial, Inc., Watertown, MA (US)

( * ) Notice: Subject to any disclaimer, the term of this patent is extended or adjusted under 35 U.S.C. 154(b) by 0 days.

(21) Appl. No.: 14/205,754

(22) Filed: Mar. 12, 2014

(65) Prior Publication Data

US 2014/0271533 A1 Sep. 18, 2014

Related U.S. Application Data

(60) Provisional application No. 61/852,158, filed on Mar. 15, 2013.

(51) Int. Cl.

| | |
|---|---|
| *A61L 24/04* | (2006.01) |
| *A61F 2/06* | (2013.01) |
| *A61B 17/12* | (2006.01) |
| *A61L 27/18* | (2006.01) |
| *C08G 18/76* | (2006.01) |
| *C08G 18/75* | (2006.01) |
| *C08G 18/77* | (2006.01) |
| *A61L 27/56* | (2006.01) |
| *C08G 18/42* | (2006.01) |
| *A61L 27/58* | (2006.01) |
| *C08G 18/61* | (2006.01) |
| *C08G 18/73* | (2006.01) |
| *A61B 17/00* | (2006.01) |
| *C08G 101/00* | (2006.01) |
| *A61F 2/82* | (2013.01) |
| *A61F 2/07* | (2013.01) |

(52) U.S. Cl.
CPC ........ *A61L 24/046* (2013.01); *A61B 17/1219* (2013.01); *A61B 17/12109* (2013.01); *A61B 17/12113* (2013.01); *A61B 17/12118* (2013.01); *A61B 17/12186* (2013.01); *A61F 2/06* (2013.01); *A61L 27/18* (2013.01); *A61L 27/56* (2013.01); *A61L 27/58* (2013.01); *C08G 18/4266* (2013.01); *C08G 18/61* (2013.01); *C08G 18/73* (2013.01); *C08G 18/755* (2013.01); *C08G 18/7621* (2013.01); *C08G 18/7671* (2013.01); *C08G 18/771* (2013.01); *A61B 2017/0065* (2013.01); *A61B 2017/00654* (2013.01); *A61B 2017/00659* (2013.01); *A61B 2017/00893* (2013.01); *A61B 2017/00898* (2013.01); *A61F 2/07* (2013.01); *A61F 2/82* (2013.01); *A61F 2250/0069* (2013.01); *C08G 2101/0008* (2013.01); *C08G 2230/00* (2013.01)

(58) Field of Classification Search
None
See application file for complete search history.

(56) References Cited

U.S. PATENT DOCUMENTS

| | | | |
|---|---|---|---|
| 2002/0072550 A1* | 6/2002 | Brady | A61L 29/06 521/155 |
| 2002/0165582 A1* | 11/2002 | Porter | A61B 17/12022 606/213 |
| 2003/0118692 A1 | 6/2003 | Wang et al. | |
| 2003/0171773 A1* | 9/2003 | Carrison | 606/213 |
| 2004/0176832 A1* | 9/2004 | Hartley et al. | 623/1.11 |
| 2005/0165480 A1* | 7/2005 | Jordan | A61B 17/12022 623/9 |
| 2006/0008419 A1* | 1/2006 | Hissink et al. | 424/45 |
| 2007/0005140 A1 | 1/2007 | Kim et al. | |
| 2007/0078506 A1 | 4/2007 | McCormick et al. | |
| 2009/0232877 A1 | 9/2009 | Montes et al. | |
| 2011/0202016 A1* | 8/2011 | Zugates | A61L 24/043 604/290 |
| 2012/0107439 A1* | 5/2012 | Sharma | A61J 1/2093 425/4 R |
| 2012/0197284 A1* | 8/2012 | Ogle | A61B 17/12036 606/195 |

* cited by examiner

*Primary Examiner* — Robert A Wax
*Assistant Examiner* — Randeep Singh

(57) ABSTRACT

Systems and methods related to polymer foams for the treatment of blood vessel dissections are generally described. Some embodiments relate to compositions and methods for the preparation of polymer foams, and methods for using the polymer foams. The polymer foams can be applied to or within a dissection caused by an intimal tear in a blood vessel, sealing the dissection and preventing further perfusion thereof. In some embodiments, the polymer foam can be formed within a body cavity (i.e., in-situ foam formation). The foam may be used to fill the dissection as a thrombosing agent. In addition, the foam may be used in conjunction with medical devices such as stents, stent-grafts, balloons, and catheters.

21 Claims, 21 Drawing Sheets

IN-SITU FORMING FOAM FOR THE TREATMENT OF VASCULAR DISSECTIONS

CROSS-REFERENCE TO RELATED APPLICATIONS

This application claims priority to U.S. Provisional Patent Application Ser. No. 61/852,158, filed Mar. 15, 2013, titled "In-situ Forming Foam for the Treatment of Aortic Dissection," which is incorporated herein by reference for all purposes.

FIELD OF INVENTION

Systems and methods relating to polymer foams for the treatment of blood vessel dissections are generally described.

BACKGROUND

Arteries are made up of three layers, the intima, the media, and the adventitia. The layer that is in direct contact with the flow of blood is the tunica intima, commonly called the intima. The next layer is known as the tunica media, or the muscular layer. The outermost layer is the tunica adventitia or the adventitia, which is composed of connective tissue. The lumen is the channel in an artery through which blood flows. A dissection is a separation in the layers of the artery wall resulting from a tear in the intima—blood flow through the tear enters the arterial wall creating a false lumen, with differing results depending on the location and unique physiology of the tear. The dissection of any of the carotid artery, vertebral artery, coronary artery, or aorta are all serious medical conditions, but even within each of these types, there is wide variability of presentations, complications, and treatments. For example, several different classification systems have been used to describe aortic dissections. The commonly-used Stanford classification is divided into two groups, A and B, depending on whether the ascending aorta is involved. A involves the ascending aorta and/or aortic arch, and possibly the descending aorta, and B involves the descending aorta or the arch (distal to right brachiocephalic artery origin), without involvement of the ascending aorta. Type A ascending aortic dissections generally require primary surgical treatment whereas type B dissections generally are treated medically as initial treatment with surgery reserved for any complications.

Where treatment with medication alone is deemed insufficient for the treatment of a dissection, the goal of surgical intervention is to treat a patient as effectively but as non-invasively as possible in order to minimize post-surgical risks and reduce recovery times. One recognized method of repairing a damaged artery is the endoscopic and endovascular placement of a stent graft or graft to repair the damaged artery. However, stents may not adequately repair the specific damage of the artery in each case, requiring more invasive procedures, or may provide only a temporary solution. A bare stent provides mechanical support for the true lumen but does not seal the intimal tear, allowing for continued perfusion of the false lumen. For example, re-intervention occurred in 81% of Complicated Type B patients in one 82 patient study. (Gotz M. Richter, *TEVAR for Acute Type B Dissections Is Not a Single Step Procedure: Permanent Surveillance and Reinterventions May Be Required*, VEITH Symposium; New York, N.Y., Nov. 17, 2011). When placed correctly, a grafted stent can cover the intimal tear, but may also occlude collateral arteries. In another example, where a stent graft was used to seal a tear or weak areas of the aortic wall, 25-50% of cases had complications with aortic branch vessels. (Fattori, R. et al., *Malperfusion Syndrome in Type B Aortic Dissection: Role of the Endovascular Procedures*, Acta Chir Belg 108 (2008): 192-197). In other circumstances a stent or stent graft can seal the primary tear, but a secondary tear will continue to allow blood flow into the false lumen. Therefore, it is desirable to provide a tool that adds additional flexibility and more varied treatment options for blood vessel dissections over known methods and tools.

SUMMARY OF THE INVENTION

Systems and methods relating to polymer foams are provided. The subject matter of the present invention involves, in some cases, interrelated products, alternative solutions to a particular problem, and/or a plurality of different uses of one or more systems and/or articles.

In one aspect, the present invention relates to a method of treating a dissection within a patient comprising: providing a medical device comprising an exterior surface, and a fluid prepolymer material, placing the medical device within a blood vessel at the site of a false lumen, delivering, into a space between the exterior surface of the medical device and the blood vessel, the fluid prepolymer material, and forming a foam from the fluid prepolymer material at the site of the false lumen upon delivery of the fluid prepolymer material. In one embodiment, the foam seals and/or partially fills the false lumen. In one embodiment, the medical device comprises a graft, stent graft or balloon.

In one aspect, the invention provides methods of treating a dissection within the blood vessel of a patient, such as an aortic dissection. Such methods preferably and effectively result in sealing and/or isolation of false lumens or other structures created by the dissection. In accordance with embodiments of the present invention, methods of treating a dissection comprise the step of forming an in-situ forming foam within the blood vessel. In certain embodiments, the foam is placed directly into the false lumen or other structure created by the dissection, or is placed over the tear or other opening between the blood vessel and such false lumen or other structure. In other embodiments, the method includes the step of placing a medical device within the blood vessel and placing the foam between the medical device and the false lumen or other structure created by the dissection. The foam is preferably formed from a material that reacts in the presence of a water-containing environment to generate a gas and expand into a foam.

In another aspect, the invention provides methods of treating a dissection within a blood vessel of a patient, such as an aortic dissection. The dissection is characterized by a false lumen in fluid communication with the blood vessel through an opening between the false lumen and the blood vessel. The method comprises the steps of placing a medical device within the blood vessel, the medical device comprising a structure having a first end, a second end, and an exterior surface between said first and second ends; and forming an in-situ forming foam between the exterior surface of the medical device and the false lumen. The in-situ forming foam is formed from a material that reacts in the presence of a water-containing environment to generate a gas.

In another aspect, the invention provides a system for treating a dissection within the blood vessel of a patient, such as an aortic dissection. Such systems are preferably and effectively used to seal and/or isolate false lumens or other structures created by the dissection. In accordance with embodiments of the present invention, the system comprises a chamber containing a composition, and a delivery device configured to deliver the composition into the blood vessel or other structure created by the dissection, and/or the tear or other opening between the blood vessel and the false lumen or other structure created by the dissection, where it is placed in contact with an initiator to thereby form a foam. In preferred embodiments, the composition is a prepolymer, the initiator is water, and the foam is a polyurethane foam.

In accordance with embodiments of the present invention, the system comprises a first chamber containing a first composition, a second chamber containing a second composition, a mechanism that places the first composition into contact with the second composition to thereby form a foam, and a delivery device configured to deliver the first and second compositions into the blood vessel, the false lumen or other structure created by the dissection, and/or the tear or other opening between the blood vessel and the false lumen or other structure created by the dissection. In preferred embodiments, the first composition is a polyol, the second composition is a multifunctional isocyanate, and the foam is a polyurethane foam.

In other aspects, the invention includes foams, compositions, formulations, products, kits, and systems that are useful for performing the methods described above.

The present invention offers advantages not previously known in the art. For example, the polymers of the invention can be deployed into a closed body cavity without requiring specific knowledge of target site(s) while nonetheless creating conformal contact with target tissues located throughout the cavity. Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Systems and methods related to the use of polymer foams to treat blood vessel dissections are generally described. Some embodiments relate to compositions and methods for the preparation of polymer foams, and methods for using the polymer foams. In some embodiments, an in-situ forming foam is used for the treatment of blood vessel dissections, such the endoscopic treatment of Type B Aortic Dissection.

In cases where blood has traveled through the intima layer to the media layer of the aorta, creating a false lumen, the foam may be used to seal the intimal tear of the aortic wall, thus preventing further perfusion of the false lumen. As used herein, the term "tear" is used to denote an opening, created by any means and of any size or shape, between the lumen of a blood vessel and a false lumen created by dissection of the blood vessel. As used herein, "lumen" means a passageway through which blood or other fluids flow. As used herein, "false lumen" means any cavity or other structure of any size or shape that is created by dissection of a blood vessel. As used herein, the foam of the present invention is said to "seal" a tear or a false lumen in that it creates an effective barrier between the lumen of a blood vessel and a false lumen created by a dissection.

Figure 12:
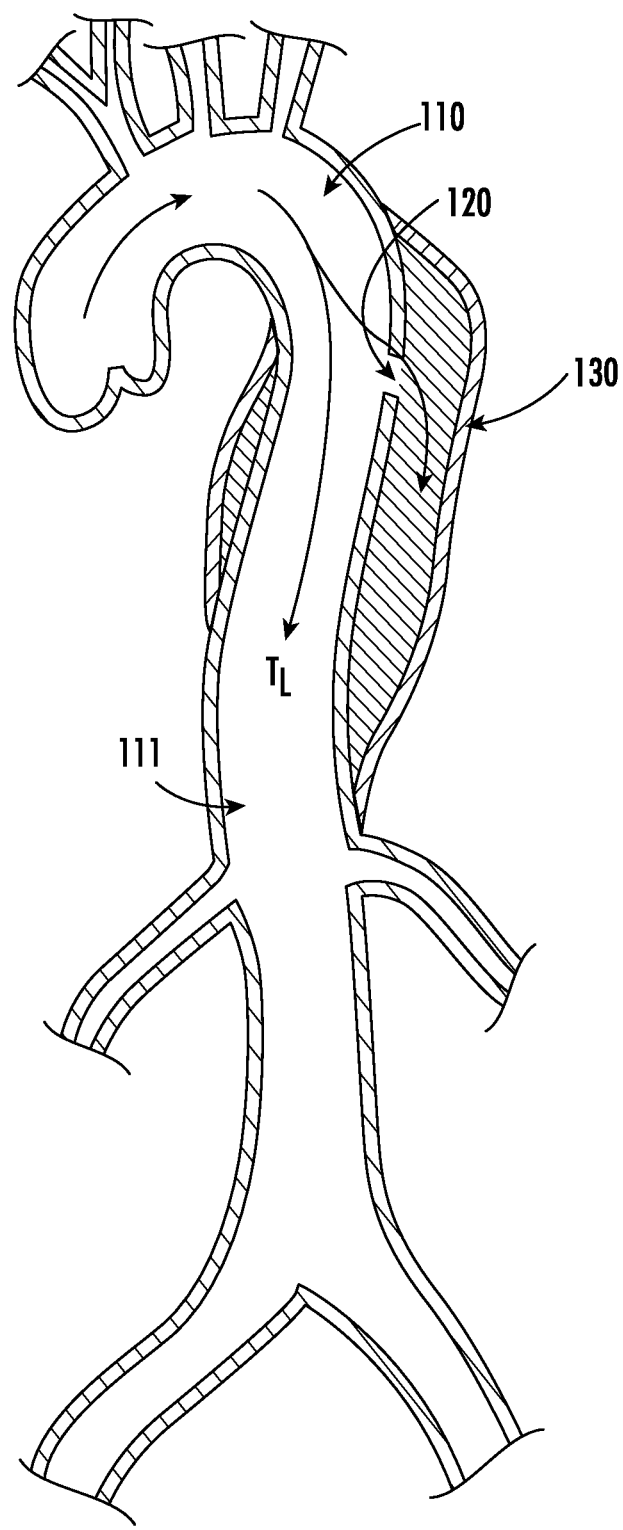
FIG. 12 includes an exemplary cross-section of a dissecting aorta.

As a non-limiting example of the medical conditions treatable by the methods and systems of the present invention, FIG. 12 shows a cross-section of a dissecting aorta 110 with an intimal tear 120 and a false lumen 130; the flow of blood through the true lumen 111 and false lumen 130 are indicated by arrows. In some embodiments, the foam of the present invention is used to partially or completely fill the false lumen 130. In other embodiments, the foam is used in conjunction with a stent, stent graft, balloon, catheter or other medical device. In still other embodiments, the foam is used to seal off select areas of a bare stent, which gives the advantage of using a stent graft without occluding visceral arteries. In all of the embodiments described herein, the foam creates a seal between the blood vessel and the false lumen, although the foam may only result in the partial filling of the tear or the false lumen.

An in-situ forming foam from a liquid precursor is injected into the aorta by endovascular access. Although the present invention is described with specific reference to treating aortic dissections as a non-limiting example, it should be appreciated that the present invention is equally applicable to the treatment of dissections occurring throughout the vasculature. As used herein a foam is said to be "injected" into a tear, lumen, false lumen or other cavity in that it is placed by any suitable means into the location indicated. In some embodiments, the polymer foams can be formed within the aorta (i.e., in-situ foam formation). The polymer foams can be injected into or onto the intimal tear of the dissection, thus sealing it off from blood flow. In another embodiment, sealing of the intimal tear with the in-situ forming foam may be followed by the placement of a stent or stent graft. In another embodiment, in-situ forming foam is injected after the placement of the stent graft, which forms a space for subsequent injection of foam. In some embodiments, the in-situ forming foam is used to selectively seal off areas of a bare stent. In other embodiments, the in-situ forming foam is injected into the false lumen. In still other embodiments, foam may induce thrombosis of the false lumen in Type B Aortic Dissection. In addition, the foamed polymers of the present invention may be capable of exerting a pressure on an internal surface of a body cavity and preventing or limiting movement of a bodily fluid (e.g., blood, etc.).

The polymer foams may possess attributes that make them particularly suitable for use within the body. For example, in some embodiments, the polymers used to form the foams described herein are preferably biocompatible. The polymers may also be biodegradable in some cases. In some instances, the polymers may be sufficiently elastic to allow for body movement while being sufficiently stiff to support body tissues. In some embodiments, the foam composition may be adjusted so that it wets tissues effectively. Furthermore, pendant groups may be attached that allow for the targeted adhesion of polymer to tissues or injured or target tissues. As used herein, "tissues" may refer to tissues in general or injured or target tissues. Functionalization of the polymer used to form the foam may also lead to covalent bonding of the foam to a surface inside the body cavity, which may aid, for example, in preventing dislocation of the foam within the cavity.

The materials and methods described herein exhibit several advantages relative to traditional methods of treating aortic dissection, as well as other types of artery dissection. In-situ forming foam gives surgeons an additional tool to repair various types of injury associated with arterial damage, for example, to ensure that an intimal tear is sealed off or a false lumen is thrombosed. In addition, the use of a stent or stent graft alone to treat dissections offers less flexibility and fewer treatment options than the methods and systems of the present invention. In a complex disease like aortic dissection every case is different, so additional flexibility may lead to improved patient outcomes. For example, foam alone or in conjunction with a stent may allow endovascular repair for patients where stenting alone is not a viable option due to a complicated dissection anatomy. In such applications the foam effectively increases the number of clinical applications of a stent and the availability of non-invasive alternatives to open surgery.

Use of foam may also reduce post-surgical complications and the need for re-interventions. For example, reinforcing a stent with the foams of the present invention may reduce the occurrence of re-intervention by more effectively sealing an intimal tear than would be accomplished by a stent alone. In another example, a degradable foam may be used to induce thrombosis of a false lumen. The foam may contain agents to promote clotting and be highly porous to offer a greater surface area, which in turn may expose the blood to more surfaces containing thrombosis agents. Full thrombosis of the false lumen is associated with recovery of the true lumen and an improved patient outcome, and spontaneous false lumen thrombosis occurrence is expected to be low.

In another exemplary advantage, a coiling silicone foam that fills a false lumen would be less likely to spread into a true lumen via reentry tears along the false lumen, and offers the additional advantage of offering a high surface area, which in turn may induce clotting or expose the blood to more surfaces containing thrombosing agents.

Additional advantages of the polymer foams described herein are described in more detail below.

Figure 13:
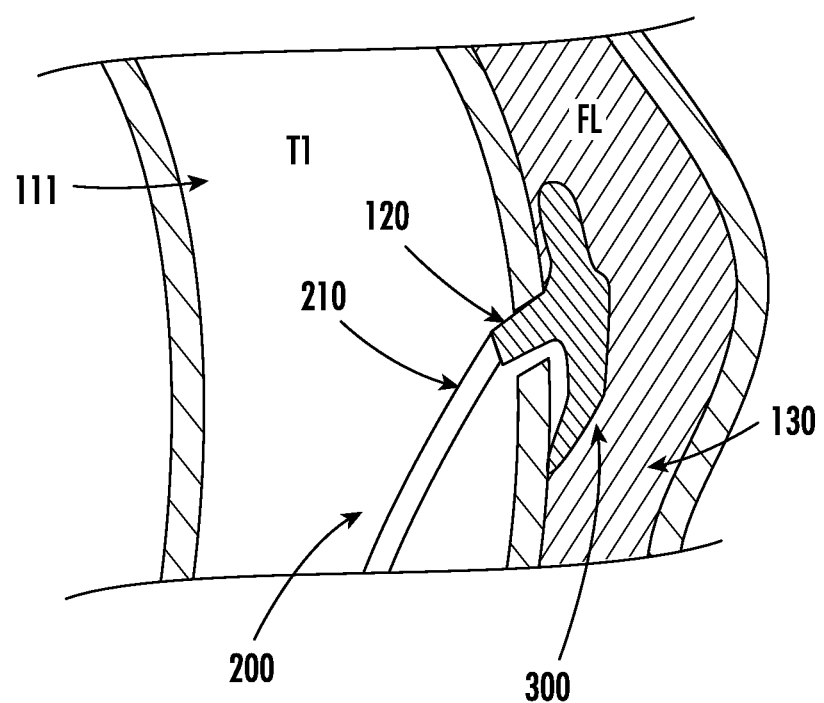
FIG. 13 an exemplary cross-section of an aortic dissection where a catheter is used to seal an intimal tear with foam.
Figure 14:
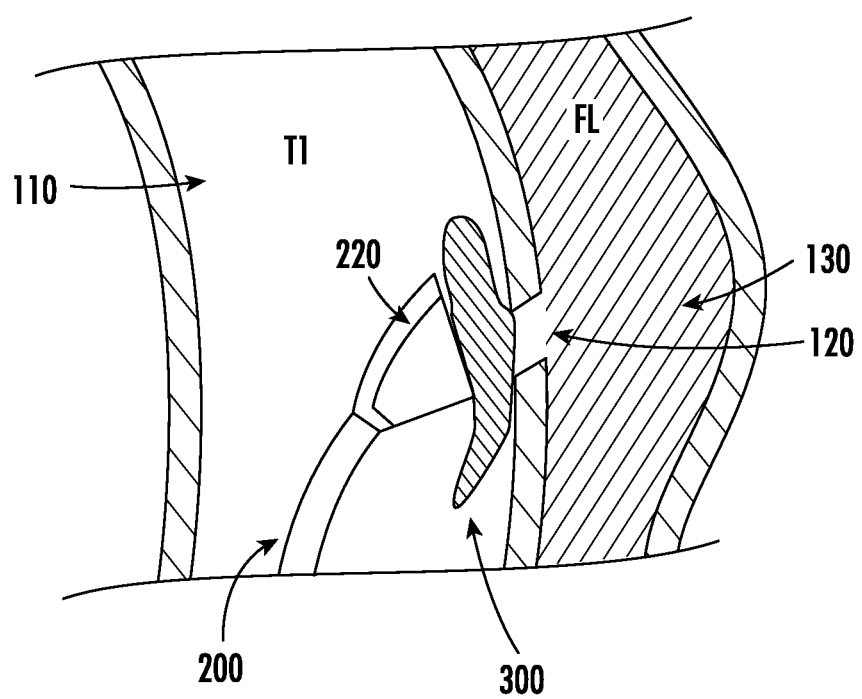
FIG. 14 includes an exemplary cross-section of an aortic dissection where a catheter with a fanned tip is used to seal an intimal tear with foam.

Polymer foams may be used in a variety of applications. In-situ forming foam may be injected into/onto the intimal tear of a dissection, thus sealing it off from blood flow. In one embodiment shown in FIG. 13, the distal end 210 of a delivery catheter 200 may be open-ended or have a small needle on the end to inject the foam 300 into/onto the tear 120. In another embodiment, an exemplary cross-section of which is shown in FIG. 14, the catheter 200 may have a fanned tip 220 to dispense the foam 300 into a thin, wide layer to achieve a seal.

Figures 15A, 15B:
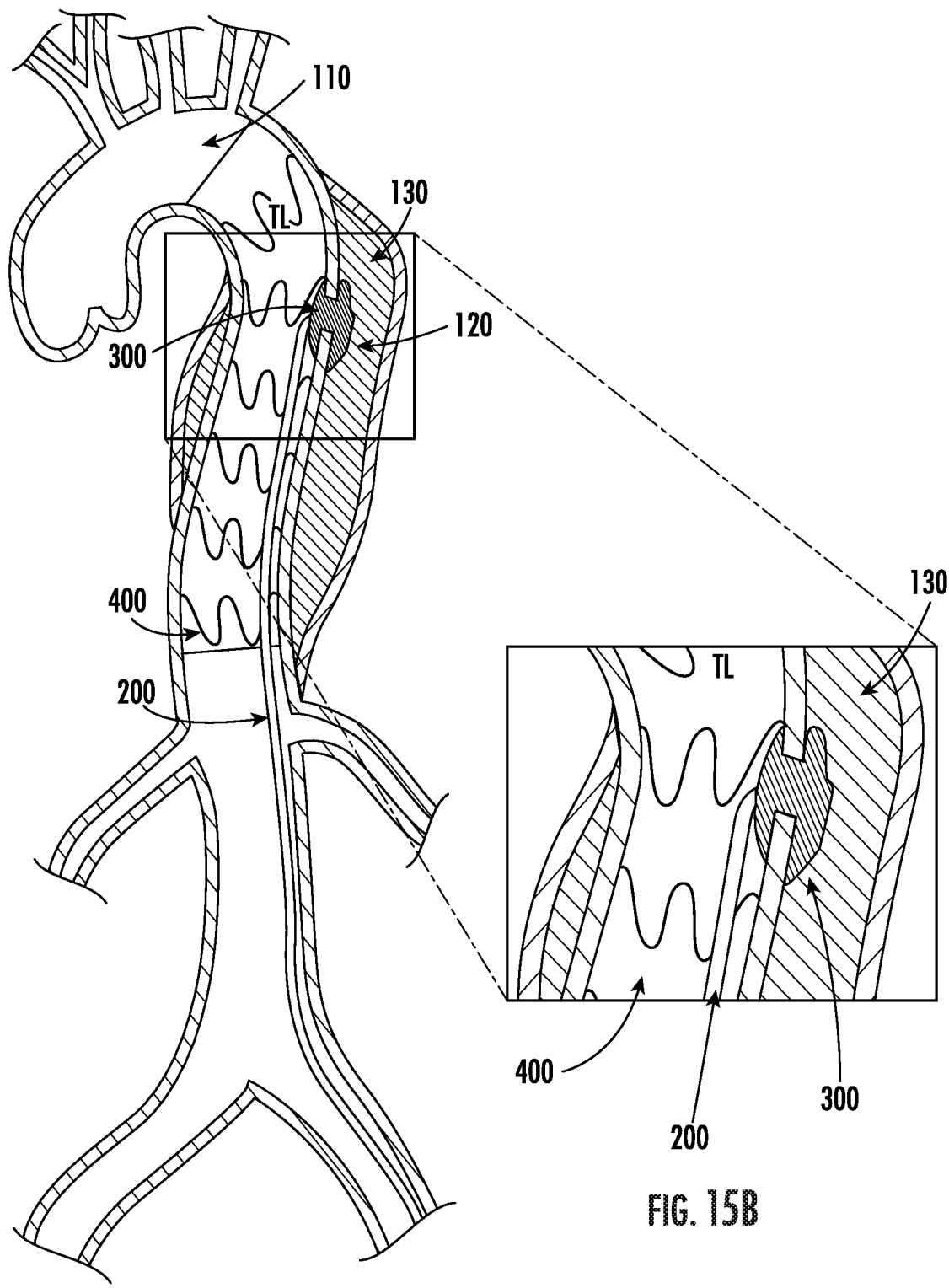
FIG. 15A includes an exemplary cross-section of an aortic dissection where a stent graft is used to provide mechanical structure to the true lumen and the false lumen is sealed with foam.
FIG. 15B includes an exemplary cross-section of an aortic dissection in close up of 20A where a stent graft is used to provide mechanical structure to the true lumen and the false lumen is sealed with foam using a catheter.

In some embodiments of the present invention, sealing of an intimal tear with in-situ forming foam may be performed in conjunction with the placement of a stent or stent graft. This is advantageous because a bare stent alone may fail to seal the intimal tear and risk further perfusion of the false lumen. When a stent is used in conjunction with foam, the tear is sealed and the stent can provide mechanical structure to the true lumen. Also, a stent graft may successfully cover the intimal tear upon placement, but move over time depending on the anatomy of the landing zone, and re-expose the tear. Further, a stent graft may occlude certain collateral arteries involved in the dissection, potentially causing ischemia and/or paralysis. Using foam as described ensures that the tear is sealed regardless of the stent graft placement or movement. As shown in the embodiments illustrated in FIGS. 15A and 15B, the in-situ forming foam 300 is injected via catheter 200 after the placement of a stent graft 400, which forms a space between the blood vessel 110 and the false lumen 130. Use of a stent-graft in this manner may help contain the foam 300 and guide it to seal the tear 120. Either a bare or grafted stent may provide mechanical stability to the true lumen and prevent the false lumen from impinging on the true lumen. A grafted stent may in addition prevent the foam in the false lumen from entering the true lumen.

Figure 16:
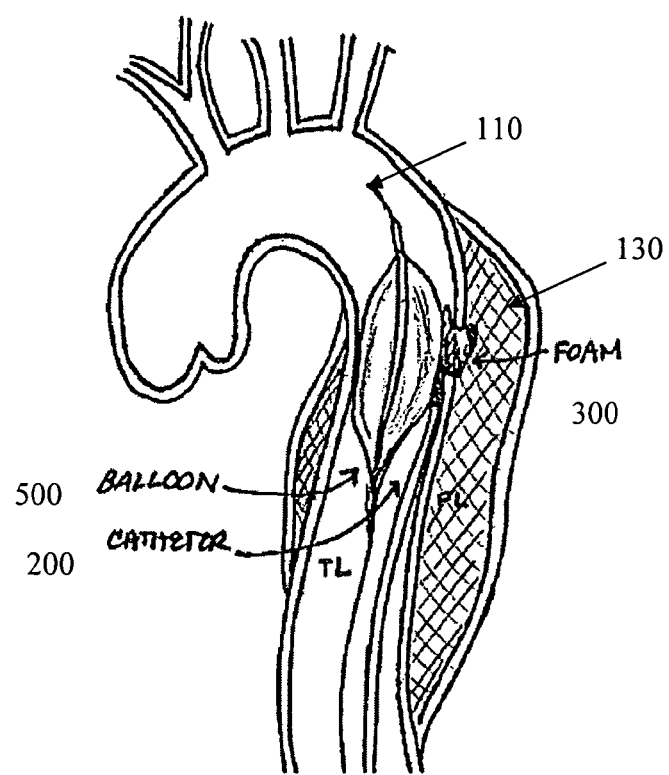
FIG. 16 includes an exemplary cross-section of an aortic dissection where a balloon catheter and a catheter are used to seal an intimal tear with foam.
Figure 17A:
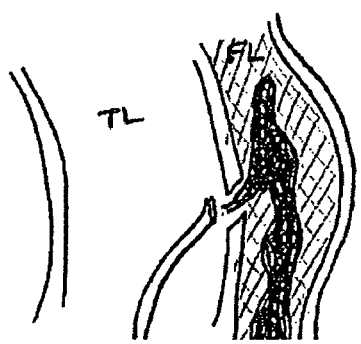
FIG. 17A includes an exemplary cross-section of an aortic dissection where a catheter is used to dispense foam from the tip.
Figure 17B:
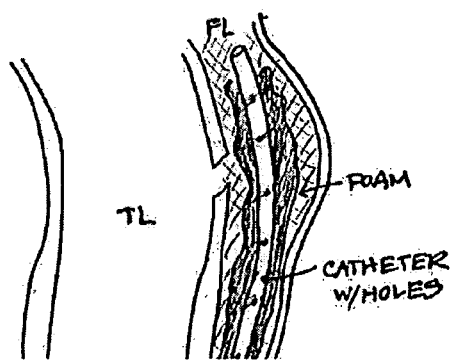
FIG. 17B includes an exemplary cross-section of an aortic dissection where a catheter with holes along its length is used to dispense the foam throughout a false lumen.

In other embodiments as shown in FIG. 16, a similar effect may be achieved by deploying a balloon catheter into the true lumen near the intimal tear, and deploying foam 300 between the balloon 500 and the tear 120. The balloon catheter may be deployed while the false lumen is filled in order to contain the foam in the false lumen, and prevent the foam-filled false lumen from impinging on the true lumen. In some embodiments the balloon catheter may be of the type that allows flow through the aorta while deployed.

Figure 18:
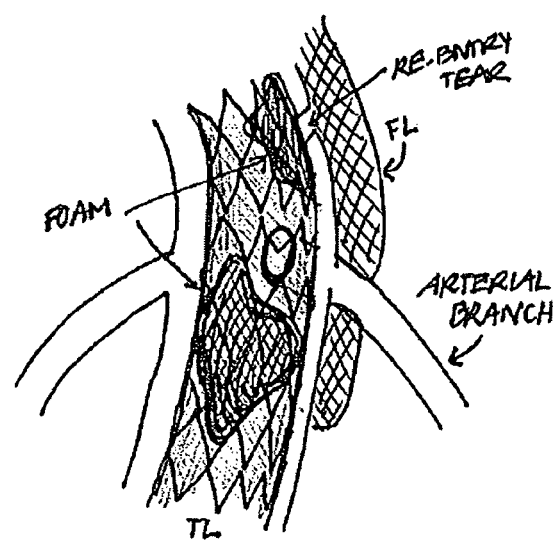
FIG. 18 includes an exemplary cross-section of an aortic dissection where foam is used to seal select areas of a bare stent; weak arterial walls and tears are reinforced while arterial branches are left unobstructed.

In other embodiments of the present invention, in-situ forming foams are used to selectively seal off areas of a bare stent. A bare stent may provide mechanical structure to the true lumen without occluding any vessel branches, but cannot seal a tear or weak aortic wall. A stent graft may seal a tear or weak areas of the aortic wall, but many cases have complications with aortic branch vessels. Selective sealing of the bare stent with foam allows reinforcement without occlusion of branch vessels as shown in FIG. 18, which can cause ischemia and/or paralysis.

An experiment has been developed in which a one-part moisture-cure formulation (AF305) was deployed into a simple aortic dissection model. AF305 comprises a custom synthesized prepolymer with isocyanate functionality, an amidine catalyst, surfactant, diluent, and solid tantalum. A rigid tube is secured to the inside wall of a flexible tube of slightly larger diameter to model the true lumen reinforced by a stent and the aorta, respectively. The space created between the rigid tube and flexible tube represents a false lumen. The model is submerged in water.

Figure 19A:
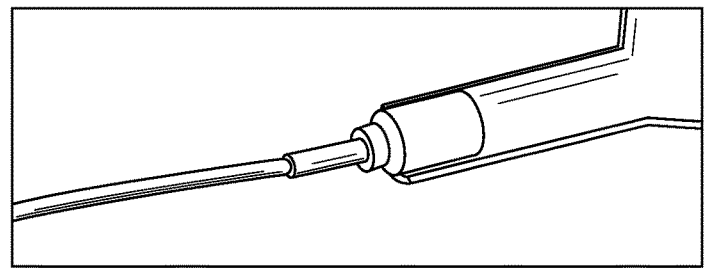
FIG. 19A shows an example of a catheter and single barrel syringe used to deploy formulations into a simple aortic dissection model.
Figure 19B:
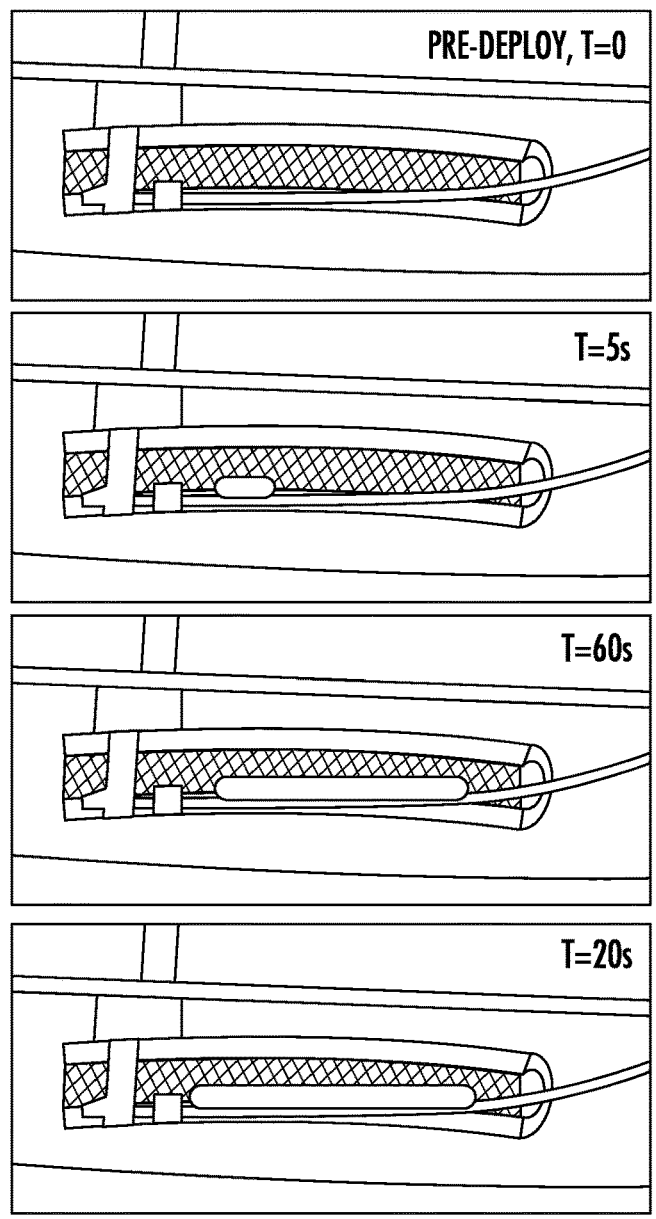
FIG. 19B shows time lapse images of the deployment of an in-situ forming foam into a simple aortic dissection model consisting of a rigid tube secured to the inside of a slightly larger flexible tube to model a true lumen reinforced with a stent and an aorta, respectively. The space created between the two tubes models a false lumen. The system is submerged in water.
Figure 20A:
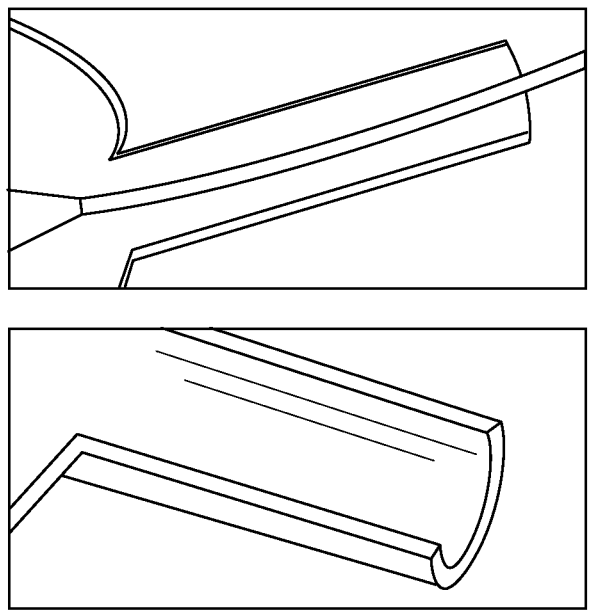
FIG. 20A shows cured foam material that has expanded into the dissection model shown in FIG. 19B.
Figure 20B:
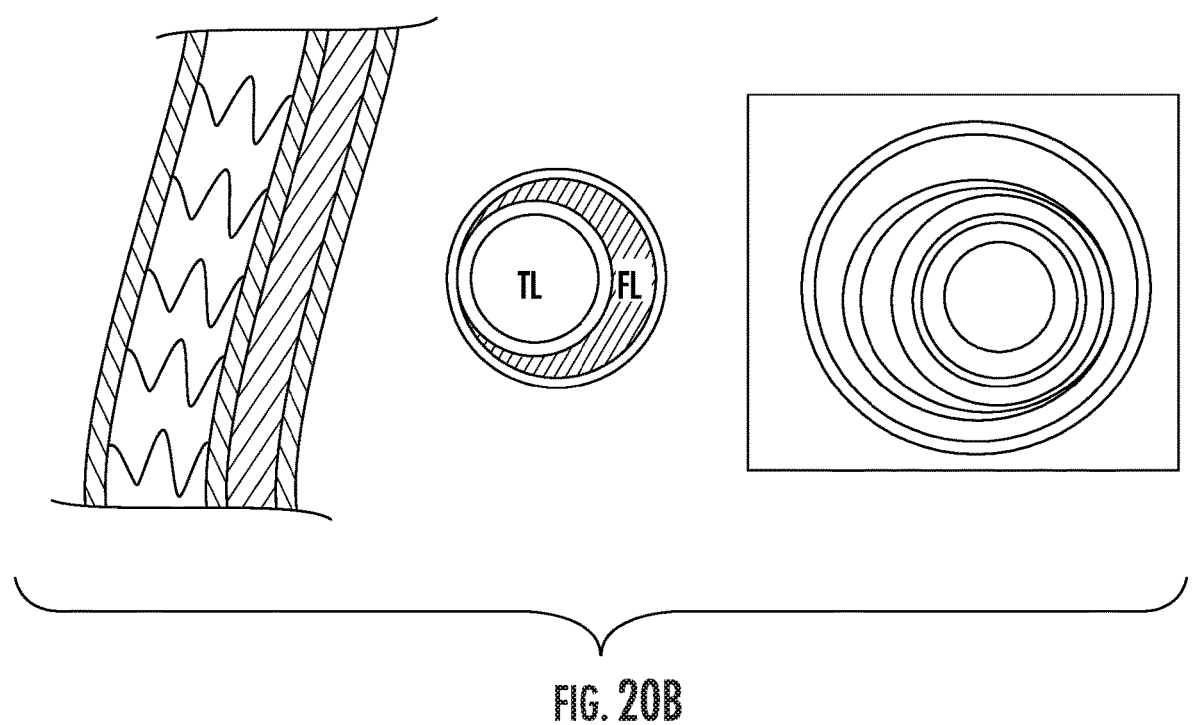
FIG. 20B shows cured foam that has expanded into the dissection model shown in FIG. 19B and has made conformal contact with the walls of the model false lumen (cross section and exemplary schematic).

The formulation was easily pushed from a syringe through a 7F catheter and dispensed the along the false lumen (FIGS. 19A and 19B). The material expanded to fill the available space and cured in approximately one minute. The material was viscoelastic, robust, and porous (FIGS. 20A and 20B). Tantalum, a radiopaque agent, was incorporated into the formulation to provide delivery visibility. There is also an opportunity to incorporate other agents into the material, such as procoagulents to promote thrombosis of the false lumen.

As can be seen from the above examples, aortic dissections are treated by the injection of in-situ forming foams into false lumens or on, at or around the tear between the true lumen of a blood vessel and the false lumen, either with or without the adjunctive use of a medical device such as a stent, stent graft, balloon catheter, or other catheter. In these or other embodiments, the foam may contain an agent to induce thrombosis or otherwise clot or fill the false lumen in whole or in part. In some embodiments the foam may be porous so as to allow for maximum surface area for blood to contact, thus inducing clotting. In some embodiments, the foam is biodegradable, which may promote thrombosis of the false lumen but not create a permanent implant.

The polymer foams may also be used to fill a body cavity created by the loss of body tissue. As used herein, "body cavity" refers to any space located within a body, such as the false lumens described herein and including spaces within the external surface of the skin. It should be noted that body cavities may be, in some cases, exposed to the external environment surrounding a body, such as, for example, in the case of an open wound or surgical incision. In some embodiments, polymer foams may be formed or located within an enclosed body cavity, for example, by placing a polymer in the body cavity and closing an incision such that the polymer or polymer foam are not exposed to the external environment. While the embodiments described herein may find particularly advantageous use for purposes of repairing Type B Aortic dissections, the use of polymer foams are not limited to these types of dissections, and may be used, for example, for the repair of carotid artery, vertebral artery, or coronary artery dissection, or for the repair of Type A aortic dissection. In the former two (cervical artery dissections), endovascular stenting has been shown to be safe and technically feasible. Drug eluting stents are used for low risk coronary artery dissections. In both cases, the in-situ forming foam system may be used in conjunction with the stent, or alone, to treat cases where a stent does not give the surgeon enough flexibility to treat the dissection. As noted above, any dissection repair using in-situ forming foam may be performed in conjunction with a bare or grafted stent. In addition, the applications noted above may be delivered through an endoscopic, open surgical, transcutaneous puncture, or other medical procedures.

Figure 1A:
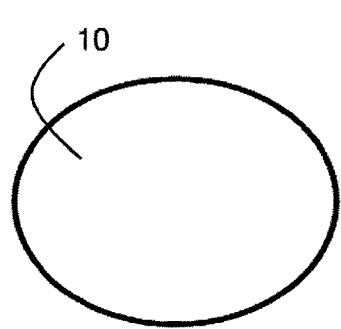
FIGS. 1A-1C include schematic illustrations of the formation of a polymer foam, according to one set of embodiments.
Figure 1B:
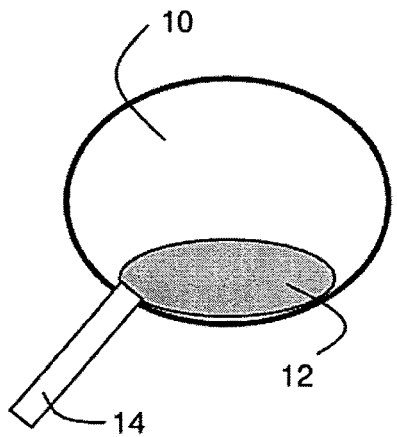
Figure 1C:
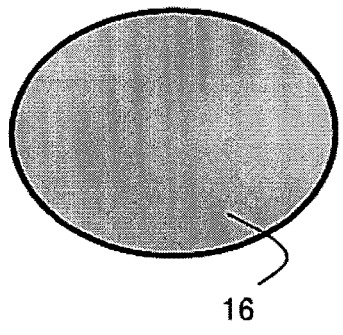

Examples of polymer foams and methods associated therewith are now provided. In particular, systems and methods for foaming a polymer to form a polymer foam are now described in connection with one set of embodiments. FIGS. 1A-1C include schematic illustrations of the formation of a polymer foam within a body cavity. As used herein, a "polymer foam" refers to an article comprising a plurality of cells (i.e., volumes) that are at least partially surrounded by a material comprising a polymer. The cells within the foam may be open or closed. The cells within the foam may be any suitable size. In some embodiments, the polymer foam may comprise at least 10 cells, at least 100 cells, at least 1000 cells, at least 10,000 cells, or more.

FIG. 1A includes body cavity 10 in which a polymer foam can be formed. In FIG. 1B, polymer material 12 is provided to cavity 10 via source 14. The polymer material can comprise a plurality of polymers which can be, for example, cross-linked to each other in the process of forming a polymer foam. In some embodiments, the polymer material comprises fluid polymers in the substantial absence of a carrier fluid. In other instances, the plurality of polymers in the polymer material are suspended in a carrier fluid (e.g., a liquid suspension medium, etc.). The term "polymer" is given its ordinary meaning in the art, and is used to refer to a molecule that includes a plurality of monomers. The terms "formulation," "prepolymer," "prepolymer formulation," and "polymer formulation" are used interchangeably to designate a polymer-based system or material capable of further reaction in a vessel or cavity. These terms can refer to a single prepolymer material, or to a prepolymer material blended with other additives (e.g., catalysts, surfactants, solvents, diluents, crosslinkers, chain extenders, blowing agents, and the like) to create a prepolymer formulation. In some embodiments, a polymer may comprise fewer than about 100, fewer than about 50, fewer than about 25, or fewer than about 10 monomer units. In some embodiments, a polymer may comprise between about 2 and about 100, between about 2 and about 50, between about 2 and about 25, between about 5 and about 50, or between about 5 and about 25 monomer units. The polymers within the polymer material can comprise a variety of functional groups that allow the polymers to, for example, cross-link to each other, attach to tissue or other material within the body cavity, interact with agents in the bloodstream of the subject (e.g., imaging agents, cross-linking agents, etc.), among other functionalities.

Source 14 may comprise any suitable source known to one of ordinary skilled in the art. In some embodiments, source 14 comprises any suitable container through which polymer material 12 may be passed. For example, in some embodiments, the source may comprise a syringe having one or more barrels through which the polymer material is flowed. In some embodiments, the source may comprise a container in which the polymer material is under pressure, and the polymer material is released from the container upon depressurizing the container (e.g., as in an aerosol can). In such embodiments, the polymer material can be applied as a spray, for example. The container may comprise several means for pressurizing known to those of ordinary skill in the art. For example, the container may be pressurized during the filling process in a manufacturing environment, or pressure may be generated immediately prior to use. In one embodiment, one or more pressure-generating chemical reactions may occur within the container, with the user initiating the reaction, waiting for pressure build-up and releasing the material. In another embodiment, pressure may be generated manually, via hand pump, crank, or rotary device. The container may also have an attachment, such as a catheter or other delivery device, which is introduced into the body that allows the material to flow into the cavity. In certain embodiments, such delivery catheters are of a size and flexibility that allows for delivery of the polymer materials described herein into a desired body cavity, preferably by endoscopy. In certain embodiments, the tip of the delivery catheter may be open-ended, fanned, or designed to spray the polymer material, thus creating different material dispension profiles. Such catheters may also have openings along the length and/or circumference to distribute the polymer in desired locations within a cavity or throughout the entire cavity.

Figure 2A:
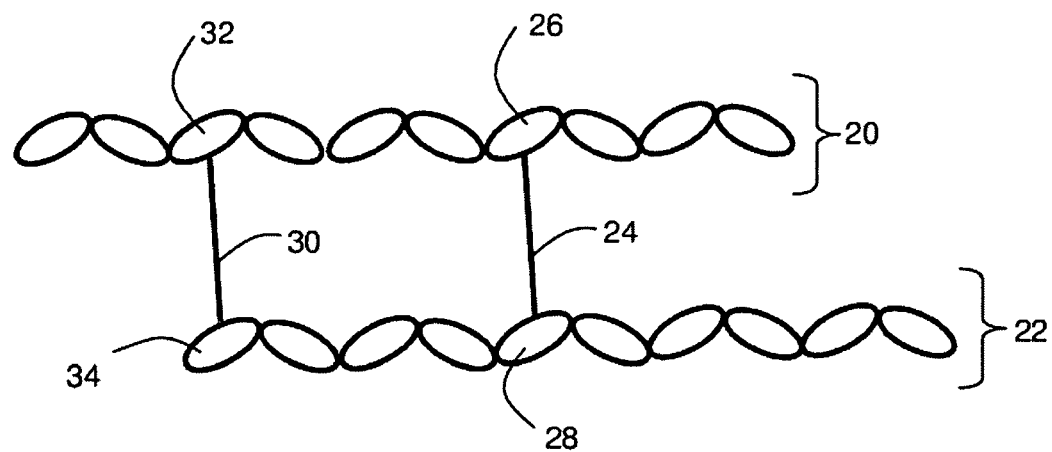
FIGS. 2A-2B include exemplary schematic illustrations of cross-linking of polymers.
Figure 2B:
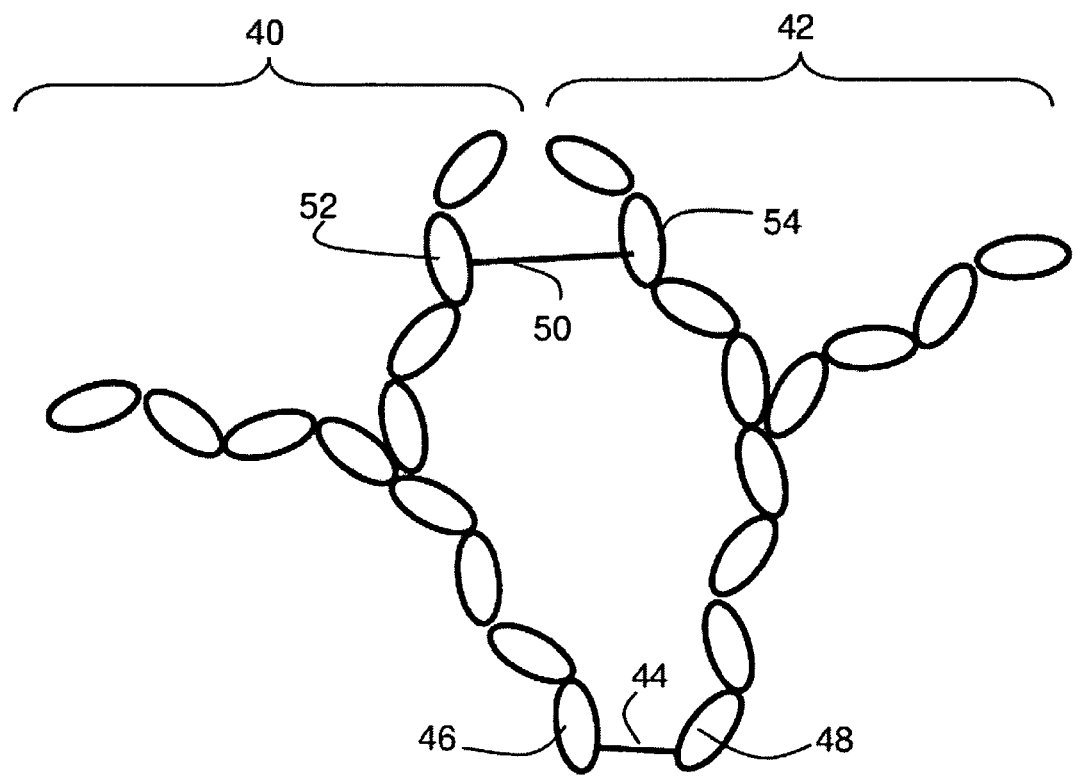

In some embodiments, the polymers within the polymer material may cross-link within the body cavity. The term "cross-linking" is used to refer to the process whereby a pendant group on a first polymer chain may react with a second polymer chain (e.g., a pendant group on the second polymer) or other molecule or molecules to form a covalent or ionic bond joining the two polymers. Polymers that can undergo cross-linking can comprise straight chains, branched chains having one or more arms (i.e., multi-arm chains), or mixtures of these. In some cases, the polymer (branched and/or non-branched) may contain reactive side chains and/or reactive terminal groups (i.e., groups at the end of a polymer chain), and cross-linking may involve reactions between the side chains, between terminal groups, and/or between a side chain and a terminal group. For example, in FIG. 2A, polymers 20 and 22 are cross-linked, with bond 24 (which may comprise a single covalent bond or a plurality of covalent bonds between multiple atoms) between monomer 26 and monomer 28. In addition, bond 30 is formed between non-terminal monomer 32 and terminal monomer 34. In FIG. 2B, branched polymers 40 and 42 are cross-linked, with bond 44 between monomer 46 and terminal monomer 48, and bond 50 between monomers 52 and 54. In some instances, the polymer material may be substantially free of polymers that comprise reactive groups on terminal monomers. In other cases, the polymer material may comprise a substantial amount of polymers with reactive groups on terminal monomers. In some embodiments (e.g., in some cases in which branched polymers are employed) a relatively large percentage of the cross-linking reactions (e.g., at least about 70%, at least about 80%, at least about 90%, at least about 95%, at least about 99%, or substantially all of the cross-linking reactions) can occur between terminal reactive groups.

Cross-linking may commence via a variety of mechanisms. In some embodiments, polymer may cross-link once the polymer contacts moisture (e.g., water, blood, aqueous solutions, etc.), for example, within a body cavity. Cross-linking may be achieved via acrylate, methacrylate, vinyl, cinnamic acid, or acrylamide groups in some embodiments. Such groups may be cross-linked via the application of ultraviolet radiation and can be used in conjunction with an external foaming agent. In some instances, a cross-linking initiator may be introduced into the subject in which the body cavity is located (e.g., via the bloodstream, via a separate container in the delivery system such that the initiator and the polymer do not mix before delivery, etc.) to initiate cross-linking of the polymer. For example, a free radical initiator, such as eosin or 2,2-dimethoxy-2-phenylacetophenone, can be used to initiate cross-linking of polymers bearing acrylate, methacrylate, or vinyl groups. Other examples of reactive groups on polymer chains that can be paired to produce cross-linking include, but are not limited to, hydroxyls and isocyanates, amines and NHS-esters, thiols and maleimides, azides and alkynes (i.e. "click chemistry"), acid chlorides and alcohols, and in a preferred embodiment, isocyanates and polyols. It may be desirable, in some embodiments, to keep these paired chemicals separate until they are introduced into the body cavity to prevent unwanted cross-linking outside the body cavity. For example, the polymer may include azide functional groups, and alkynes can be introduced to the body cavity from a container separate from the container used to introduce the polymer. In some embodiments, these chemistries are also employed in conjunction with an external foaming agent. As the polymer material cross-links, its viscosity may be increased. In some cases, the cross-linking proceeds until a substantially solid material (e.g., a solid elastomeric foam) is formed.

Referring back to the example in FIG. 1, polymer material 12 (and/or a cross linked or partially cross-linked product of the polymer material) is foamed to form polymer foam 16, as illustrated in FIG. 1C. The foam may be formed, for example, by introducing a gas into the polymer material. Once the gas is supplied to the polymer, the gas may be dispersed within the polymer (e.g., as bubbles) to form the cells of the foam. The dispersion of gas within the polymer may lead to expansion of the polymer such that it substantially fills the body cavity, as shown in FIG. 1C. In some cases, the foaming step may involve self-expansion of the polymer, for example, when gas is generated by a hydrolysis reaction or as a byproduct of a reaction between functional groups on different polymer chains. Thus, cross-linking and foaming may take place substantially simultaneously in some embodiments. The self-expansion of the foam may drive the polymer into interstitial regions of the dissected artery that otherwise may be difficult to reach. In addition, the self-expanding foam may provide internal compression against the walls of the dissected artery.

In some embodiments, the foaming step is not dependent upon the cross-linking step to form a foaming gas. For example, the foaming step may occur due to an introduction of gas separate from the polymer material. In some cases, gases comprising air, $CO_2$, or other materials may be introduced into the body cavity via an external source (e.g., a syringe or any other suitable container). This gas may then permeate the polymer material (or a cross-linked product) to form bubbles within the material, which may form the voids in the foam as polymeric material cross-links around them. In cases where the gas is supplied via an external source, the source of the gas may be the same as or different from the source of the polymer material (e.g., 14 in FIG. 1).

In some embodiments, the gas may be supplied as a product of a chemical reaction of part of the polymer or a cross-linked product. For example, in some embodiments, the foaming step comprises reacting one or more pendant groups on the polymer or cross-linked product to form a gaseous product. The gas-producing pendant groups may react upon contact with another material in the body cavity. For example, in some cases, the gas producing groups may react upon contact with moisture in the body cavity. In some cases, the gas-producing pendant groups may react with a chemical supplied to the body cavity separately from the polymer material (e.g., via the bloodstream, via an external source separate from the polymer material source, etc.). In some embodiments, the gas-producing pendant groups on the polymer chain may react with another component that is supplied to the body cavity. In some embodiments, the polymer or cross-linked product may comprise $CO_2$-producing groups. Examples of $CO_2$-producing groups include, but are not limited to, isocyanate groups, carbonates, bicarbonates, and carbamates. Such groups may produce $CO_2$ gas when reacted with an acid, for example. In some cases, the $CO_2$-producing group may include an N-hydroxysuccinimide carbonate, illustrated below:

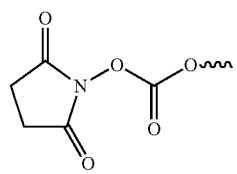

$CO_2$-producing groups may include, in some cases, imidazole carbamates, as illustrated below:

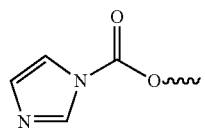

As noted above, in some embodiments, the foaming and cross-linking steps occur substantially simultaneously. In some cases, the foaming and cross-linking steps may occur substantially simultaneously, but remain independent of each other. For example, the polymer material may cross-link by reacting with water in the body cavity, and, at substantially the same time, gas may be introduced to the polymer material from an external container. In another embodiment, a first material containing gas generating groups may produce gas by contact with a second agent (e.g., water in the body, water supplied separately, or chemical additive), while contact or interaction with a third material leads to crosslinking. For example, at the time of delivery, polymer A with isocyanate groups can be mixed with water and polymer B, in which the former causes the generation carbon dioxide to foam the material and polymer B can contain hydroxyl groups that react with isocyanates on polymer A to form a crosslinked network between polymers A and B.

The foaming and cross-linking steps may be, in some cases, part of the same reaction process. For example, one or more reactions may produce a gaseous by-product which serves as the supply of gas to form the polymer foam, but concurrently leads to the generation of new functional groups that enable crosslinking. The gaseous by-product can be trapped within the polymer and coalesce to form bubbles. As the reaction progresses, the formation, growth and expansion of the gas bubbles can expand the polymer volume and force it into interstitial areas of the body cavity. As the polymer cross-links, a three-dimensional foam can be formed within the body cavity. The volume expansion and cross-linking can serve to coat and seal surfaces of the body cavity, and optionally provide internal compression, which may be useful, for example, in stopping the flow of blood. In addition, such a reaction scheme can be combined with an external supply of gas (e.g., $CO_2$ in an external container) to increase the amount of gas contained in the polymer or a cross-linked product of the polymer.

Figure 3:
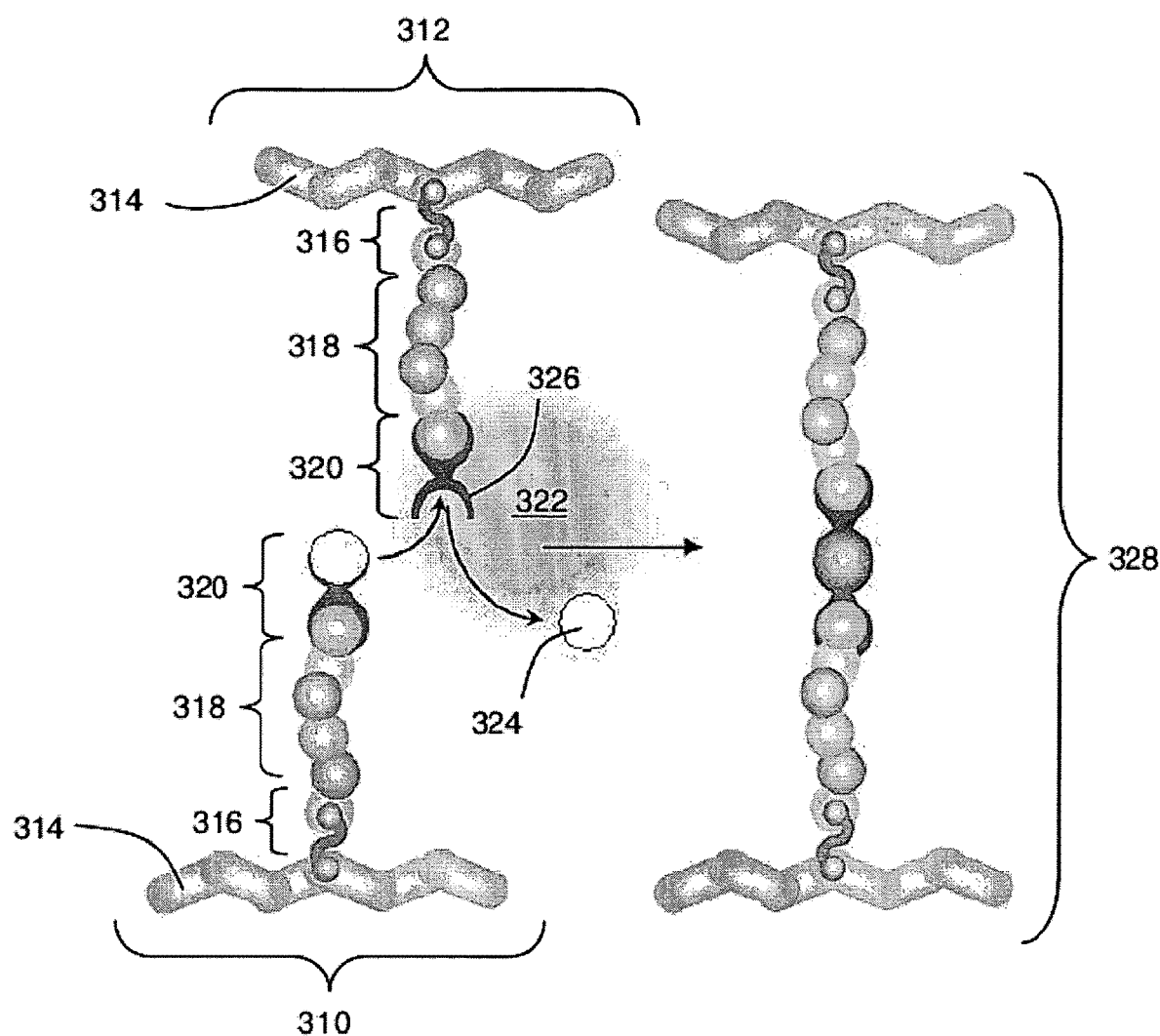
FIG. 3 includes a schematic illustration of cross-linking and gas generation, according to one set of embodiments.

FIG. 3 includes an exemplary schematic diagram of a system in which simultaneous cross-linking and gas generation occur. Polymers 310 and 312 include biodegradable backbones 314. The polymer may also comprise a linker region 316 to attach pendant groups. The polymer may also comprise a targeting ligand 318 which can be used to bond the polymer to desired sites (e.g., damaged tissue). In addition, the polymer in FIG. 3 includes a cross-linking site 320 that can simultaneously solidify and foam the material. When the polymer is exposed to a compound 322 (e.g., water) in the body cavity, gas 324 is released from the cross-linking site, which generates a functional group 326 that can react with another polymer to produce a cross-linked structure 328.

All of the foaming mechanisms described herein may occur before any substantial cross-linking has occurred or during cross-linking of the polymer material or a cross-linked product of the polymer material. For example, in some cases, an external gas may be introduced into and dispersed within a polymer material that has not substantially cross-linked. The polymer material may then cross-link around the bubbles to form the foam. In such cases, the viscosity of the polymer material can be chosen such that the material is able to retain bubbles within the volume without the need for cross-linking. In some embodiments, at least some cross-linking may occur before the gas is introduced to the polymer material, and the gas is dispersed within a partially cross-linked polymer material that has not completely solidified to form a foam.

Cross-linking and/or foaming may be achieved, in some instances, using isocyanate chemistry. Isocyanate groups are relatively unstable when exposed to water and moisture. Exposure of isocyanate groups to water or moisture (or other compounds) can lead to the decomposition of the groups, cross-linking of polymers to which they are attached, and release of carbon dioxide, as shown below for a model lysine isocyanate:

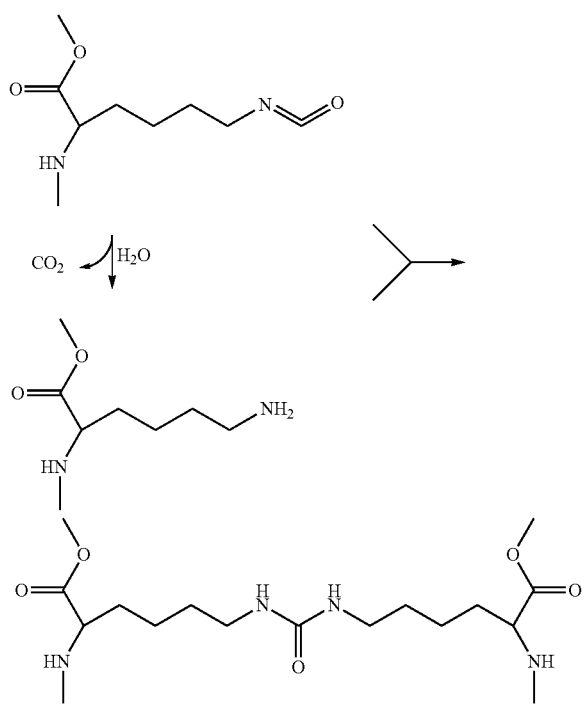

In the mechanism above, the isocyanate is partially hydrolyzed to produce amines, which can react with native, non-hydrolyzed isocyanates, as shown above. Not wishing to be bound by any theory, a cross-linked structure can be produced because the rate of the amine-isocyanate reaction may be on the order of or faster than the rate of isocyanate hydrolysis, and inter-chain reactions occur between these functional groups to ultimately form a cross-linked structure. The isocyanates on the polymer can also react with amine groups of the tissue (e.g., lysines in proteins), which can form a covalent bond with the tissue to further strengthen the seal. In addition, the isocyanate hydrolysis reaction produces $CO_2$, enabling simultaneous cross-linking and gas production in a single-reaction scheme.

In certain embodiments, polyurethane foams may be generated by cross-linking polyols with multifunctional isocyanates. Polyols suitable for use in such embodiments include polyether- and polybutadiene-based polyols. Polyols of particular interest include polypropylene glycol (PPG) and polyethylene glycol (PEG), as well as random and block copolymers thereof. Also suitable for use are polycarbonates, polybutadienes, and polyesters. Diols, triols, and tetrols are most preferred, but multifunctional polyols with any suitable number of arms may be used. Molecular weights between 100 and 10,000 Da are preferable, with molecular weights up to 6,000 Da being most preferred, and blends of polymers with different molecular weights, degrees of branching, and composition are often used. Commercial polymers of particular interest include polypropylene glycols (425, 1200 Da), polyethylene glycols (200, 400, 600, 1000, 2000, 3000 Da), Pluracol products (355, 1135i, 726, 816), Arch Poly-G 30-240, Poly-G 76-120, Poly-G 85-29, trimethylolpropane ethoxylate (450, 1014 Da), pentaerythritol ethoxylate (797 Da), UCON 75-H-1400, UCON 75-H-9500, poly(ethylene glycol)-block-polypropylene glycol)-block-poly(ethylene glycol) copolymers, dipropylene glycol, diethylene glycol, tripropylene glycol, triethylene glycol, tetrapropylene glycol, tetraethylene glycol, trimethylolpropane ethoxylate (170, 450, 730, 1014 Da), hydroxyl terminated polydimethylsiloxanes, and carbinol (hydroxyl) terminated polydimethylsiloxanes. In certain embodiments where the foam is formed from a two-part system, it is preferred that polyols used in the present invention comprise an amine catalyst in an amount up to 10 pphp, a water content of up to 20 pphp, a surfactant in an amount up to 10 pphp, and a diluent up to 300 pphp (preferably up to 250 pphp and most preferably up to 15 pphp). In certain embodiments where the foam is formed from a one-part system, it is preferred that polyols used in the present invention comprise an amine or metal catalyst in an amount up to 10 pphp, a surfactant in an amount up to 10 pphp, and a diluent up to 300 pphp (preferably up to 100 pphp and most preferably up to 10 pphp).

Isocyanates suitable for use in such two-part systems include any polymeric isocyanate with a degree of functionality greater than 2.0, with the most useful range being 2.0-2.7. Preferred polymeric isocyanates are based on methylene diphenyl isocuanate (MDI). Isocyanate true-prepolymers and quasi-prepolymers may also be used. In this case, a "quasi-" prepolymer, or semi-prepolymer, is a polymer formed by the reaction between a multifunctional isocyanate and polyol, where the isocyanate-to-alcohol ratio is greater than the stoichiometric two-to-one ratio. A "true-" prepolymer, or strict-prepolymer, is a polymer formed by the reaction between a multifunctional isocyanate and polyol, where the isocyanate-to-alcohol ratio is equal to the stoichiometric two-to-one ratio. In this embodiment, aliphatic isocyanates are preferred, such as hexamethylene diisocyanate (HDI) and isophorone diisocyanate (IPDI).

In some instances, it may be advantageous to position isocyanate groups in the polymer so that it is accessible for hydrolysis and cross-linking, without inhibiting binding to the tissue (e.g., damaged blood vessels). In one set of embodiments, a lysine group in the targeting peptide can be converted to an isocyanate by reaction with diphosgene. In some instances, the isocyanate and peptide chemistries can be completely decoupled by modifying a fraction of the side chains with peptide while the balance are modified with isocyanate.

The polymer that is foamed to form the polymer foams described herein may be formed using a variety of chemistries. In some embodiments, the polymer comprises a synthetic polymer. As used herein, a "synthetic polymer" refers to a polymer that is a product of a reaction directed by human interaction. For example, synthetic polymers can include polymers synthesized by reactions of natural or synthetic monomers or combinations thereof that are directed by human interaction. The formation of synthetic polymers can also include chain elongation of natural or synthetic polymers. In some embodiments, the synthetic polymer is not found in nature. In other cases, the synthetic polymer can be found in nature, but the polymer is synthesized via human interaction (e.g., in a laboratory setting). In some embodiments, the polymer may comprise a poly alpha-hydroxy acid. In some cases, the polymer may comprise a polyester. In some cases, the polymer may comprise a polyether-polyester block copolymer. In some cases, the polymer may comprise a poly(trimethylene carbonate). In some embodiments, the backbone of the polymer can exclude at least one of polynucleotides, proteins, and polysaccharides.

In some embodiments, the polymer foam is formed by cross-linking a condensation polymer of a polyol and a polyacid. The terms "polyol" and "polyacid" are given their standard meanings in the art, and are used to refer to compounds comprising at least two alcohol groups and at least two acidic groups, respectively. Examples of polyols suitable for use in forming the condensation polymer used to form the polymer foams described herein include, but are not limited to, glycerol, polyethylene glycol, polypropylene glycol, polycaprolactone, vitamin B6, erythritol, threitol, ribitol, arabinitol, xylitol, allitol, altritol, galactritol, sorbitol, mannitol, iditol, lactitol, isomalt, and maltitol, wherein the functional groups present on the polyol are optionally substituted. Examples of polyacids suitable for use in forming the condensation polymer used to form the polymer foams described herein include, but are not limited to, succinic acid, fumaric acid, a-ketoglutaric acid, oxaloacetic acid, malic acid, oxalosuccinic acid, isocitric acid, cis-aconitic acid, citric acid, 2-hydroxy-malonic acid, tartaric acid, ribaric acid, arabanaric acid, xylaric acid, allaric acid, altraric acid, galacteric acid, glucaric acid, mannaric acid, dimercaptosuccinic acid, oxalic acid, malonic acid, succinic acid, glutaric acid, adipic acid, pimelic acid, suberic acid, azelaic acid, sebacic acid, malic acid, or vitamin B5, wherein the functional groups present on the polyacid are optionally substituted.

In some embodiments, the condensation polymer may comprise poly(glycerol-sebacate) (PGS). An exemplary synthesis pathway in which glycerol and sebacic acid are used to form PGS is shown below:

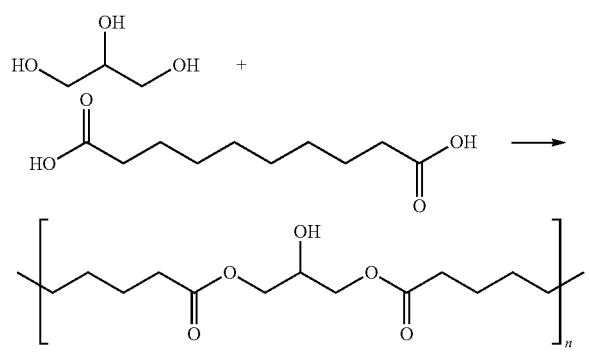

In some embodiments, the polymer foam is formed by cross-linking a polymer comprising the following formula (I):

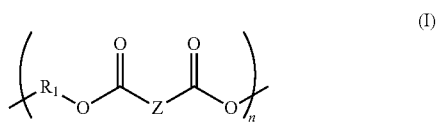

wherein R1 and Z can be the same or different and each is an alkyl, heteroalkyl, alkenyl, heteroalkenyl, alkynyl, heteroalkynyl, aryl, heteroaryl, heterocycle, acyl or carbonyl group, any of which may be optionally substituted, and wherein n is an integer greater than 1. In some embodiments, R1 and/or Z are substituted with a gas producing group. For example, R1 and/or Z may be substituted with a $CO_2$-producing group (e.g., isocyanate).

In some embodiments, the method can comprise cross-linking a polymer comprising the formula (II):

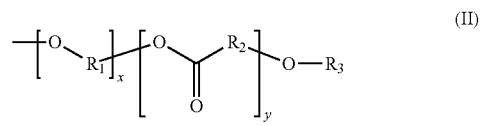

wherein $R_1$ and $R_2$ can be the same or different and each is an alkyl, heteroalkyl, alkenyl, heteroalkenyl, alkynyl, heteroalkynyl, aryl, heteroaryl, heterocycle, acyl or carbonyl group, any of which may be optionally substituted; wherein x and y are non-negative integers; wherein $R_3$ may be a hydrogen, gas generating functional group, or tissue binding domain.

In some embodiments, the polymer may comprise the poly(lactic acid) (PLA), poly(glycolic acid) (PGA), and polycaprolactone (PCL) class of polymers and their copolymers, such as poly(lactate-co-caprolactone) or poly(glycolate-caprolactone). Copolymerization of the lactide, glycolide and caprolactone monomers in various ratios can yield materials with a wide range of mechanical properties, thermal characteristics and degradation times. The structure of the PLA/PGA/PCL copolymers (and associated properties such as molecular weight, etc.) can be tailored, in some cases, by adjusting the type of initiator used and its molar ratio with the monomer(s).

In some embodiments, the polymer comprises poly(glycolate caprolactone). In some cases, the PGCL composition includes a ratio of glycolide to caprolactone of about 50:50. An exemplary synthesis pathway for PGCL is shown below, in which pentaerythritol is used as an initiator to form 4-armed, branched structures.

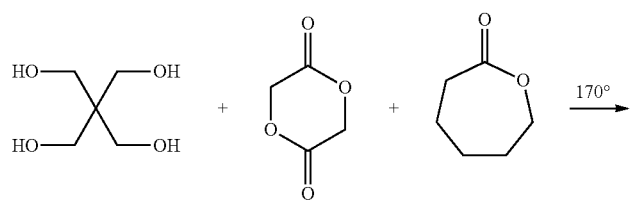

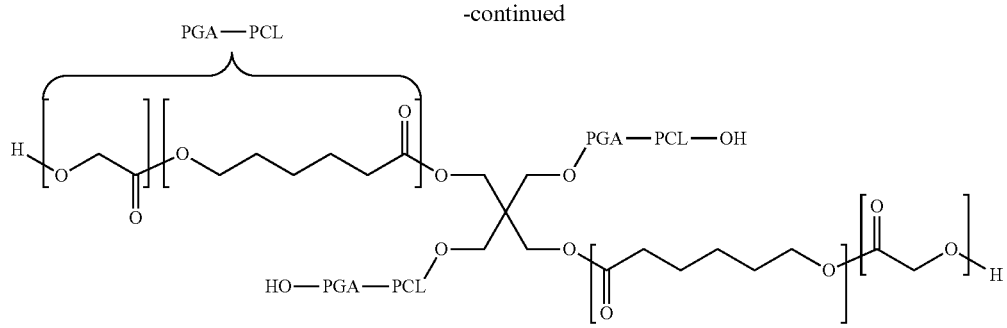

The properties of the polymer used to form the polymer foam may be tailored to achieve a desired result. In some embodiments, an in-situ forming foam from a liquid precursor is injected into the aortic dissection by endovascular access. The foam may be a two part polyurethane system, with a polyol containing phase and an isocyanate (NCO) containing phase that react upon mixing. A mixing element may be placed between the cartridge containing the liquid precursors and the catheter to initiate the reaction. Kinetics may be controlled with catalysts or the reactivity of the polymer end groups, and may be tailored to fit the procedure.

In some embodiments, the foam may be a polyurethane prepolymer with NCO functionality, which reacts upon contact with moisture or heat. These initiators may be provided by the body or the delivery system. The hydrophilicity/hydrophobicity of the foam may be controlled by the nature of the soft segment of the prepolymer. The structural integrity of the foam may be controlled by the hard segment of the prepolymer, the molecular weight of the soft segment, and functionality. Kinetics may be controlled with catalysts or the reactivity of the functional groups.

In some embodiments foam may be engineered to adhere to the tissue, in order to form a better seal of a tear. This may be achieved by controlling the hydrophobicity of the foam; more hydrophobic materials have been shown to promote protein adhesion. This may also be achieved by functionalizing the surface with mucoadhesives such as poly vinyl pyrrolidone (PVP), methyl cellulose (MC), carboxymethylcellulose (CMC) or other cellulose derivatives. NCO itself at the prepolymer ends may covalently bond to tissue surface.

In some embodiments the foam may contain a radiopaque agent to allow visualization as it moves through a catheter towards a target area, and as it seals and/or fills a target space. For example, radiopaque agents may include tantalum, barium sulfate, water-soluble iodinated contrast agents, oily contrast agents, zirconium dioxide, or other contrast agents known in the art.

As discussed above, in some embodiments the foam may contain an agent to induce thrombosis of the false lumen; such agents may include thrombin, chitosan, montmorillonite clays, kaolin, diatomaceous earth, zeolite, cellulose, collagen I-XXIX, gelatin, fibrin, fibrinogen, or other agents known in the art.

As discussed above, in some embodiments the foam may be porous so as to allow for maximum surface area for the blood to contact, thus inducing clotting. The porosity of the foam can be controlled with the surfactant, blowing catalyst, and NCO index.

As discussed above, in some embodiments the foam may be biodegradable. Biodegradable foam may be achieved by using a biodegradable polymer soft segment, including, for example, polycapralactone, polyglycolide, polylactic acid, or polyanhydrides.

In some embodiments, the viscosity of the polymer is tailored such that the polymer is able to permeate the dissected artery and create conformal contact. An overly viscous polymer may require excessive pressure to deploy within the dissected artery. In addition, an overly viscous polymer may inhibit the polymer from accessing interstitial spaces. An overly low-viscosity polymer might be difficult to contain the material to the target site or may be displaced by the flow of a bodily fluid. One of ordinary skill in the art will be able to produce the desired viscosity for a given polymer type by, for example, adjusting the molecular weight of the polymer. In some embodiments, the viscosity and the molecular weight are related through a power law. The molecular weight of a polymer may be adjusted by, for example, controlling the time of the polymerization reaction used to generate the polymer. In some embodiments, the molecular weight of the polymer is between about 1000 and about 10,000 g/mol or between about 1200 and 6000 g/mol. The viscosity of a polymer may be adjusted by, for example, adding diluents such as any suitable low molecular weight, low viscosity compound, examples of which include triacetin, propylene carbonate, tetraethylene glycol dimethyl ether, dimethyl esters of diacids (e.g., diethyl malonate, dimethyl adipate), dimethyl sulfoxide, and oils (vegetable, olive, castor, etc.). In embodiments that include polyols, it is preferable to add up to about 300 pphp of diluent to control polymer viscosity.

In some embodiments, the polymer is amorphous or semi-crystalline with a glass transition temperature ($T_g$) below room temperature. Such properties yield, in some cases, polymers with sufficiently low viscosities that they can be dispensed from an external container via pressure-driven flow.

In some embodiments, properties or composition of the polymer may be chosen to achieve a desired hydrophilicity or hydrophobicity. The hydrophilicity of the polymer may be selected, in some instances, such that the surfaces (e.g., tissue surfaces) within a body cavity are appropriately wetted. Generally, a material with increased hydrophilicity will have a greater tendency to wet soft tissues surfaces. However, the polymer and resulting polymer foam may be, in some cases, somewhat hydrophobic such that they do not dissolve into biological fluids. Appropriately hydrophilic polymers are capable of conformally wetting interior surfaces of a body cavity while remaining contained within the cavity. In some embodiments, the composition of the polymer may be selected to achieve a desired hydrophilicity. For example, in some embodiments, the chain length of a monomer used to synthesize the polymer can be varied to change hydrophilicity. As a specific example, the carbon chain length between carbonyl groups of a diacid monomer can be varied from between two and eight aliphatic carbons, producing a range of hydrophilicity in the resulting polymer. In another example, the ratio of PEO to PPO groups in the polymer can be varied to control hydrophilicity, where a greater ratio of PEO to PPO groups will promote hydrophilicity whereas a greater ratio of PPO to PEO groups will promote hydrophobicity.

In some embodiments, the polymer foams described herein may have favorable mechanical properties. In some embodiments, the polymer foams are elastomeric. The term "elastomer" as used herein, refers to a polymer that can return to the approximate shape from which it has been substantially distorted by an applied stress. In some cases, the elastomeric polymer foams described herein may comprise a polymer having a bulk modulus of between about 0.05 MPa and about 10 MPa; 0.05 MPa and about 100 MPa; and 0.05 MPa and about 500 MPa. Elastomeric polymers may be particularly suitable for use in making polymer foams because they are capable sustaining stress without permanently deforming, while providing adequate support for body organs and tissues.

The time required to form the polymer foam after exposure to the dissected artery and the final mechanical and physicochemical properties of the polymer foam can depend on such factors as the composition of the polymer, the density of pendant groups (e.g., cross-linking groups), and relative positions of the pendant groups (e.g., cross-linking groups). One of ordinary skill in the art will be capable of adjusting the concentration and location of pendant groups to produce polymer foams with desirable physical properties.

In some embodiments, the polymer or polymer foam may be biodegradable. As used herein, "biodegradable" describes materials that are capable of degrading down to oligomeric or monomeric species under physiological or endosomal conditions. The phrase "physiological conditions," as used herein, relates to the range of chemical (e.g., pH, ionic strength) and biochemical (e.g., enzyme concentrations) conditions likely to be encountered in the intracellular and extracellular fluids of tissues. In some embodiments, the physiological pH ranges from about 7.0 to 7.4. In some embodiments, biodegradable materials are not hydrolytically degradable but can be fully degraded via enzymatic action to fully degrade. In some cases, biodegradable materials are hydrolytically or enzymatically degradable, or combinations thereof.

The polymer or polymer foam may be biocompatible, in some instances. One of ordinary skill in the art can determine biocompatibility based upon the ISO-10993 standard. For example, PGS is known to satisfy the ISO-10993 standard for biocompatibility. In some embodiments, chemical modifications (e.g., attachment of a pendant group, etc.) to the PGS backbone do not alter its biocompatibility. In some embodiments, a polymer that produces known, but acceptable levels of inflammation may be used. Examples of such polymers include poly-alpha-hydroxyacids (e.g., polylactide, polyglycolide, and polycaprolactone) and poly(trimethylene carbonate).

In some embodiments, the foam of the present invention is described to be "lava like" in that it is viscous yet flowable and hardens from its exterior surface towards its interior. The external skin of the foam forms as a fast-forming, robust, balloon-like outer layer that encases the polymer formulation, promotes material cohesion, and resists deformation and movement into collateral vessels or outside the targeted area. As the foam expands this external skin may deform, exposing some of the interior material which the reacts upon contact with the external environment to reform the external skin. The outer layer may be characterized as a "skin" in some embodiments that consists of a thin exterior layer that is more hard or solid, or less flowable, than the material contained by the outer layer. Moreover, the skin may be characterized as being "robust" because it has mechanical properties (e.g., strength, toughness, etc.) that are different, at least for some period of time, to the material contained by the skin. The interior of the material hardens more slowly via the same or a secondary process, as compared to the skin. In some cases where the skin forms rapidly, the material is not cohesive in-situ, resulting in a continuous, packable polymer, which may tend to form as a coil. Through continued extrusion of the material out of a delivery device such as a catheter or microcatheter, the user can create a long coil to partially or completely fill an aneurysm space or other bodily cavity. The space may be filled with an aneurysm coil or other medical implant and an in-situ forming foam or an aneurysm coil that is coated with a material that expands to form a foam coating in-situ. The continuous, long aspect ratio of the coil and cured outer surface prevents the coil from entering the collateral vessels to a significant degree, which could lead to adverse events. These and other factors are important distinctions and advantages of in-situ forming foams over systems and methods that make use of pre-formed foams.

In a preferred embodiment, the foam is formed by a fast cross-linking reaction that can be surface triggered by in-situ water. Multi-functional moisture sensitive silanes are one example of materials susceptible to such reactions especially when formulated with tin, titans or other metal-organic catalysts. One-part cross-linking systems can be created by a two-step process. In the first step, hydroxyl containing siloxanes (either silanols or carbinols) are reacted with an excess of multifunctional silane containing acetoxy, oxime, alkoxy (e.g., methoxy, ethoxy), isopropenoxy, amide, amine, aminoxy, or other functional groups containing silane with the hydrolytically susceptible Si—O—C bond. The resulting prepolymers have multiple groups that are susceptible to hydrolysis. In the second step, such prepolymers are exposed to in-situ water to result in a rapidly cross-linking elastic solid. The reaction proceeds from the outside-in, resulting in a quickly formed outer skin and, in some cases, the formation of the foam into a coil-like configuration. The slower permeation of water or alternative reaction trigger can be used to slowly cure the material inside of the skin. The proteins and pH of the blood can be used to support coil formation by modifying the rate of the skin-forming reaction as well as in coating the formed coil and preventing coil sticking and agglomeration upon self-contact.

Additionally, hydride functional (Si—H) siloxanes or isocyanate functionalized carbinols can be introduced into silanol elastomer formulations to generate gas and produce expanding foamed structures. Expansion of the material can be used to increase the size of the formed coil effectively decreasing coil embolization potential. Expansion of the material can also be critical to increase material size without delivery of more material, in adding porosity and in generating sealing or pressure. Additional formulation ingredients such as surfactants can be used to the impact of generated gas on porosity and expansion.

Alternatively, isocyanate-containing prepolymers are a second example of materials that may be used to generate in-situ forming coils or lava-like foams. Isocyanate groups are relatively unstable when exposed to water and moisture.

One-part isocyanate based cross-linking systems can be created by a two-step process. In the first step, polyols, diols, diamines, polyamines, diepoxides, silanols, carbinols or polyepoxides are capped with aliphatic or aromatic diisocyanates such as isophorone diisocyanate (IPDI), hexamethylene diisocyanate (HDI) and methylene diphenyl diisocyanate (MDI). Additionally, multifunctional isocyanates such as HDI biuret, HDI trimer, and polymeric MDI can be combined with multifunctional alcohols or multifunctional amines. The resulting prepolymers have multiple distant isocyanate groups that are able to react with water and amines found in blood. In the second step, such prepolymers are exposed to in-situ blood resulting in rapid cross-linking and foam formation. The reaction is water-triggered and proceeds from the outside-in, forming a porous outer skin, lava-like shell core structure that assists in coil formation. The expansion of such materials can be important in generating coils of a large diameter while maintaining a small cross-sectional area of the delivery device. Such materials can be used to form stand-alone foaming or gelling coils or combined with each other such that one material is coaxially formed on top the other. For example, a coaxial delivery device can deploy a coil forming formation surrounded by a highly expandable coating formulation. The two formulations may be from different chemistry classes. Alternatively, the two formulations may be selected to be immiscible such that upon delivery the formulations phase separate (e.g., oil miscible and water miscible formulations) to naturally form a coaxial structure. Additionally, the interaction with the catheter wall and/or the density differential of the two fluids can be used to further drive the phase separation. Additionally, two part formulations may be designed such that the two parts are not fully miscible. A surfactant system may be used to formulate the two part formulation into a single stable emulsion. Such an emulsion could be delivered via single chamber delivery device and does not require mixing. The emulsion can be destabilized by shear during delivery or in-situ factors (pH, temperature, ionic strength). Upon such destabilization, the internal phase of the emulsion would spill out and trigger the reaction with the external phase resulting in in-situ foam formation.

The solidification of interior portions of foams that form with an exterior skin can be controlled, for example, by altering the permeability of the material to solidification trigger. In the case that the trigger is water, permeability can be controlled by adjusting material hydrophobicity. Additional ingredients can be added to adjust material radiopacity, density, and/or contact angle with blood, tissue, or other biological matrices.

The polymeric foams described herein may be used, in some embodiments, to prevent or limit the movement of a bodily fluid within the body cavity (i.e., dissected artery), relative to an amount of movement of bodily fluid that would occur under essentially identical conditions in the absence of the polymer foam. "Essentially identical conditions," in this context, means conditions that are similar or identical other than the presence of the polymer foam. For example, otherwise identical conditions may mean that the body cavity is identical, the conditions within the cavity are identical, but where no polymer foam is located within the body cavity. In some embodiments, the polymer foam may be used to restrict the flow of blood within the false lumen, or as a barrier between the true and false lumens to restrict flow into the false lumen. In some embodiments, preventing or limiting the movement of bodily fluid comprises immobilizing and/or stabilizing blood clots. Preventing or limiting the movement of a bodily fluid may comprise, in some instances, the movement of bodily fluids into the cells of the polymer foam. Such movement of fluid into the cells may aid in the formation of, for example, blood clots or other stabilizing structures within the foam.

The movement of bodily fluids may be prevented or limited over a relatively long period of time. For example, in some embodiments, the polymer foam can prevent or limit movement of a bodily fluid within the body cavity for at least about three hours, at least about 24 hours, at least about one week, at least about one month, at least about one year, or permanently.

In some cases, the movement of bodily fluids may be prevented or limited via the application of pressure. For example, the formation of the polymer foam may involve volumetric expansion of the polymer. In some embodiments, the expansion of the polymer may result in the application of a pressure to a surface within the body cavity.

In some embodiments, the polymer foam may be used to reduce the amount of fluid movement in a dissected artery relatively quickly. In some cases, the polymer may be designed to cross-link quickly, for example, by tailoring the polymer to have functional groups that crosslink quickly, by adding catalysts, or by other known means. Suitable catalysts for use in embodiments of the present invention include amine based compounds, preferably tertiary amines, triethylenediamine (TEDA, DABCO, DABCO 33-LV), bis(2-dimethylaminoethyl)ether (Niax A1), trimethylaminoethylethanolamine, 1,2-dimethylimidazole, 1,8-diazabicycloundec-7-ene, and metallic catalyst, preferably tin octoate and/or bismuth neodecanoate. In addition, the pores of the foam can trap blood and allow it to coagulate in stagnant areas. In addition, the rate at which the amount of fluid movement is reduced can be controlled by adjusting the amount of reactive pendant groups.

In addition to gas-forming pendant groups, other active agents may also be included as pendant groups on the polymer. For example, the polymer foam can include groups used to stimulate desirable cellular responses such as fibroplasia, angiogenesis and epithelialization. In some embodiments, the polymer or polymer foam may be covalently bonded to a surface within the body cavity, for example, through a pendant group. This could be adventitious, for example in sealing a tear in the intimal layer of a blood vessel.

In some embodiments, the polymer or cross-linked product may comprise at least one pendant group (e.g., at least one pendant group) that can bind to tissue or injured or target tissue (e.g., diseased tissue, inflamed tissue, bleeding tissue, exposed media or adventitia, etc.) within the body cavity. The binding of the pendant groups to the tissue can be covalent or non-covalent. The tissue may comprise one or more molecules that would not be present in or near uninjured or nontargeted tissue as is the case, for example, when subendothelial surfaces are exposed. By including such pendant groups, a polymer or cross-linked product could be made that selectively binds to tissue or injured or diseased tissue, in comparison to uninjured or undiseased tissue. Such binding may help create a better seal of the target cavity, in some embodiments. Examples of chemicals that may be targeted by pendant groups on the polymer or polymer foam include, for example, von Willebrand Factor, collagen (e.g., collagen I and IV), a fibroblast growth factor, laminin, elastin, localized coagulation factors in their activated form (e.g., fibrin, thrombin, factor Xa, etc.), among others. Example of types of pendant groups that may be bound to the polymer or polymer foam for such uses include, for example, peptides, carbohydrates (e.g., oligosaccharide sequences) and aptamers.

One of ordinary skill in the art will be able to identify other compounds in tissue and perform screening tests to determine suitable pendant groups that could be used to bind with those compounds. For example, in vivo screening, for example by phage display technology, of a large library of possible pendant groups (e.g., permutations of peptide sequences fused to a phage surface protein, a collection of carbohydrate molecules, etc.) could be performed (e.g., in rodents) to identify pendant groups that bind specifically to the media or adventitia layers of arterial walls. The pendant group could then be identified (e.g., via sequencing for peptides) and subsequent testing (e.g., in vivo testing in uninjured animals) could be performed to verify selective binding to the injured arterial wall.

In some cases, human protein targets can be used to find pendant groups that bind selectively to the targeted site. For example, human fibrin, which is generally present where injuries to blood vessels have occurred, can be used for screening, potentially mitigating the risk present in the in vivo approach where there could be sequence and conformational differences between animal and human targets. Binding levels to fibrin can be assessed using, for example, fluorescently tagged molecules, and compared against, for example, fibrinogen, a precursor of fibrin that is ubiquitous in blood plasma. The pendant groups showing highest selectivity to fibrin over fibrinogen could be selected for use in the polymer composition.

In addition to targeting tissues, pendant groups may be used to stabilize tissue. For example, pendant groups (e.g., $CO_2$-forming groups) may covalently bond to tissue, in some cases, which may lead to the sealing of one or more openings within a body cavity. Such binding can aid in limiting or preventing the movement of bodily fluid within the dissected artery or secure the sealing of the dissected artery, in some cases. In some embodiments, the concentration of isocyanate in the polymer or a cross-linked product can affect the extent to which binding between the polymer and tissue occurs. Specifically, increasing the isocyanate levels can serve to increase and reinforce the polymer-tissue contact area, potentially producing a stronger and longer-lasting seal. Increasing the level of isocyanate in the polymer can also increases the crosslink density, potentially resulting in a more rigid material that may break more easily at the polymer-tissue interface (e.g., when the body is moved). Therefore, the concentration of isocyanate may be selected, in some cases, to balance between these two effects.

In some cases, non-isocyanate pendant groups may be used to stabilize the polymer-tissue interface. For example, the polymer may comprise aldehyde reactive groups, which can be used, for example to bind tissue proteins. Aldehyde groups may be attached by, for example, attaching ethanolamine to the polymer, followed by oxidizing the pendant hydroxyl group to form an aldehyde group. In some instances, pendant groups that selectively bind to fibrin may be used to stabilize the clot-polymer interface. In addition, pendant groups may be selected that compete with plasminogen and its activators for fibrin binding sites, blocking the activation of fibrynolytic cascade.

In some embodiments, the polymer (or the compounds used to make the polymer) are chosen such that they comprise one or more pendant hydroxyl groups. The hydroxyl groups may serve, for example, as sites at which pendant groups are attached to the polymer. For example, glycerol and sebacic acid both contain hydroxyl groups that may be used to impart functionality to PGS. As a specific example, pendant peptides can be introduced onto polymers using a two-step reaction scheme in which the polymer hydroxyl groups are first activated with carbonyldiimidazole (CDI) and then coupled to the amine-terminus of the peptide, as shown below. This chemistry can result in high coupling efficiencies.

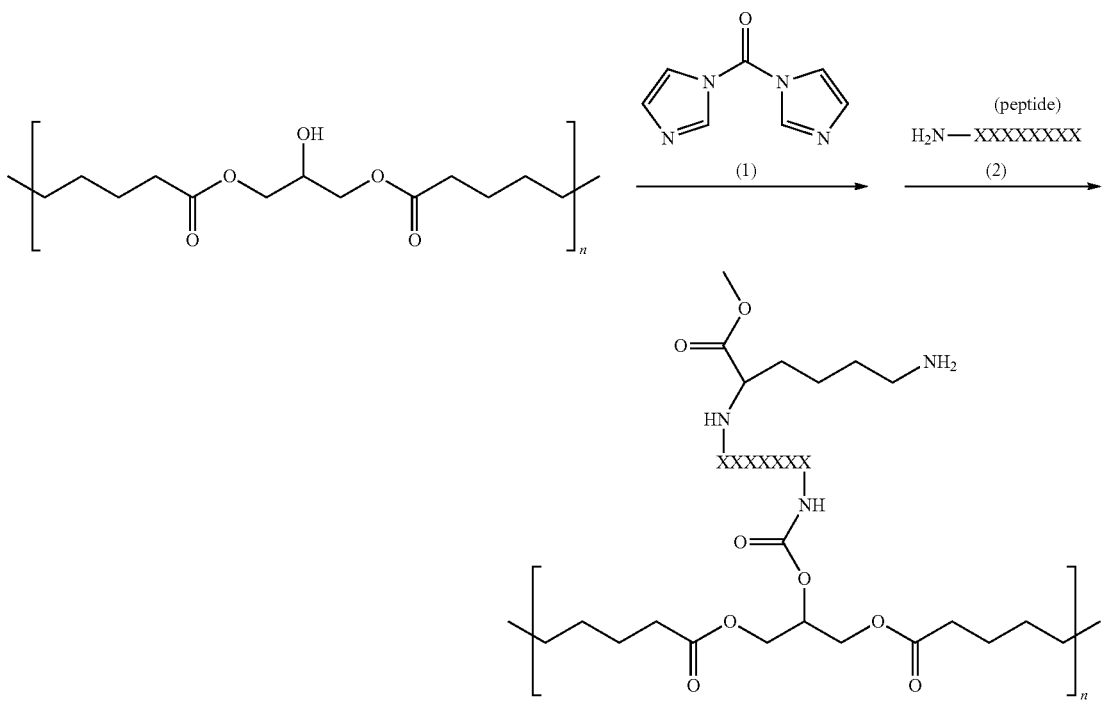

In some instances, a drug may be delivered to the body cavity with the polymer. In some embodiments, the polymer may comprise a drug. For example, a drug (or a plurality of particles containing one or more drugs) may be dispersed within the polymer. Example of such drugs include, but are not limited to, antifibrinolytic compounds (e.g., aminocaproic acid, tranexamic acid, etc.), fibrotic compounds, anti-microbial compounds (e.g., antibiotics), anti-inflammatory compounds, pro-inflammatory compounds, analgesics, pro-coagulant compounds, growth factors, and vasoconstrictors. Drugs that comprise amine groups may, in some cases, be isolated from isocyanates within the polymer, for example, to prevent unwanted reaction during the cross-linking step. Isolation can be achieved by encapsulating drugs into secondary particles and loading them into the polymer at the time of delivery to the body cavity. In addition, encapsulation may be used to release the drugs at a controlled rate. In some embodiments, a drug may be incorporated into a fiber, which may be included in the polymer. The drug release rate from the fiber can be controlled by varying composition and structure (e.g., thickness or other dimension, presence of sheath) of fiber. For example, the fiber can be designed to deliver an initial burst release shortly after the deployment of the polymer, followed by sustained delivery (e.g., over the time period in which the polymer foam will be left in the body cavity).

The polymer may be combined with a second agent (and, optionally, a third agent, fourth agent, etc.), in some cases, before or after the polymer is transported to the body cavity. The second agent may comprise, for example, a compound that accelerates at least one of cross-linking and foaming, relative to a rate of at least one of cross-linking and foaming that would have occurred in the absence of the second agent. For example, in some embodiments, the second agent may comprise an amine (e.g., a polyamine). The amine compound may serve to increase the rate at which the polymer cross-links, which may also reduce the amount of time required to reduce or eliminate the movement of a fluid (e.g., blood) or create a seal within the body cavity. The second agent may comprise, in some cases, at least one of lysine, spermine, spermidine, hexamethylenediamine, polylysine, polyallylamine, polyethylenimine, and chitosan. In some cases, the second reagent may comprise a carbonate or a bicarbonate which may be used, for example, to produce $CO_2$ gas in-situ, as described above. In some embodiments, the second reagent can comprise an acid which may be used, for example, as a reactant in the $CO_2$-producing reaction. The acid functionality may comprise, for example, a carboxylic acid pendant group attached to a polymer chain or blended with a polymer to form a mixture. In some cases, the second reagent can be native in the body (e.g., bicarbonate in the blood). In other cases, the second agent may originate from outside the body cavity. For example, the second agent may be, for example, supplied to the body cavity along with the polymer.

In some embodiments, the combination of the second agent with the polymer produces a polymer foam with significantly different mechanical properties (e.g., elastic modulus, yield strength, breaking strength, etc.) than would have been produced in the absence of the second agent. For example, addition of the second agent may lead to increased cross-linking among polymer molecules, potentially producing a stiffer foam.

The combination of the second agent with the polymer may, in some embodiments, prevent or limit blood flow within the dissected artery, relative to an amount of blood flow that would occur under essentially identical conditions in the absence of the second agent. In some embodiments, blood flow may be reduced due to the increased rate of cross-linking or foaming mentioned above. In some cases, the second agent may comprise a pro-coagulant compound (e.g., thrombin, fibrinogen, factor X, factor VII).

The second agent may be stored in a container separate from the polymer, for example, to prevent unwanted reaction between the polymer and the second agent outside the body cavity. In some embodiments, a container can be used that keeps the polymer and the second agent separated while stored or transported, but allow for mixing at the outlet nozzle or within the body cavity when the contents are expelled. The outlet nozzle can mix multiple components (>2) including gases in a static or dynamic manner. Examples of static mixers are Low Pressure Drop (LPD) mixers, Bayonet mixers and Interfacial Surface Generator (ISG) mixers. Examples of dynamic mixers are impellers, and rotary static mixers. Nozzles will handle low and high pressure differentials during dispensing. The container may also be designed to mix the components immediately prior to dispensing by breaking the barrier between each of the components and allowing them to mix. Mixing can occur manually such as shaking the canister or chambers can be under vacuum and when the barrier is broken a vortex will be created to mix the components.

In another embodiment, additives can be added to the polymer that absorb the heat generated during the cross-linking reaction. For example, materials in the form of micro or nano-particles, spheres or fibers can absorb the heat by undergoing a phase change (e.g., melting) or glass transition and thereby reduce the heat absorbed by biological tissues. For example, biodegradable fibers made of polycaprolactone can melt at ~60° C., absorbing the generated heat and reducing tissue damage.

In some embodiments, the body cavity can be imaged. The ability to image the body cavity can allow for efficient localization and repair of an injury, stabilization, identification of diseased tissue, etc. In some embodiments, pendant groups on the polymer or polymer foam can be utilized to aid in imaging the body cavity. For example, a contrast agent can be introduced into the blood stream of a subject in which the body cavity is located, and the contrast agent may be capable of selectively binding to pendant groups of the polymer. Examples of contrast agents include, for example, colored, fluorescent, or radio-opaque imaging entities. In some embodiments, the contrast agent may be added to the formulation. For example, a radiopaque polymer such as tantalum is suspended in the formulation, resulting in a radiopaque polymer foam that can be imaged. In some embodiments, the contrast agents emit electromagnetic radiation in the near-infrared range (e.g., about 700 to about 1000 nm) upon interacting with the polymer foam. As a specific example, quantum dots (QD) may be used as contrast agents. In some cases, fluorescent organic tags (e.g., fluoroscein isocyanate) or radio-opaque chelating groups (e.g., Gd3+) can be used with appropriate imaging equipment. In another example, the contrast agents listed above may be attached as pendant groups to the polymer or dispersed in the polymer to aid in visualization.

Figure 4A:
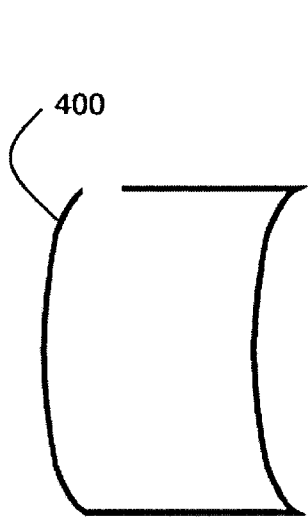
FIGS. 4A-4C include exemplary schematic illustrations of the formation of a polymer foam.
Figure 4B:
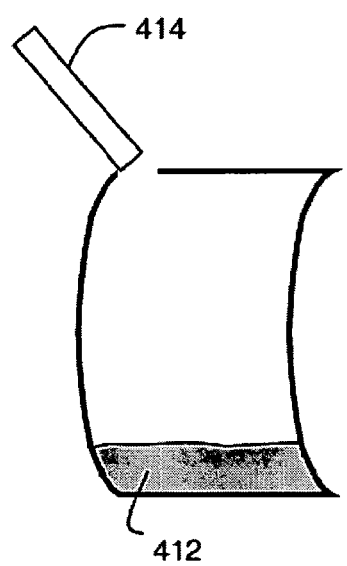
Figure 4C:
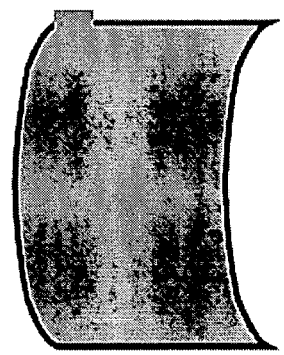

In some embodiments, the polymer foam is not formed within the body cavity, but rather, the foam is formed outside of a body cavity, and is later inserted into the body cavity. For example, FIGS. 4A-4C include schematic illustrations of the formation of a polymer foam within a mold. In FIG. 4A, mold 400 is illustrated. FIG. 4B illustrates the step of supplying polymer 412 to the mold via source 414. FIG. 4C illustrates the expansion of the polymer to form a polymer foam upon supplying a gas to the polymer. The polymer may, in some case, expand to conform to the shape of the mold. The molded polymer then may be inserted into a body cavity. In still further embodiments, the polymer may be formed into a polymer foam outside of a body cavity and without the use of a mold. The polymer foam may then be formed into an appropriate shape by using an appropriate method such as, for example, cutting, grinding, or any other suitable method.

In another embodiment drug-loaded objects are incorporated in the foam or gel at or before administration. Incorporation of drug-loaded objects into a polymer during administration is accomplished by those methods known to those skilled in the medical and pharmaceutical formulation arts. Examples of drug-loaded objects include: microspheres, microfibers, core-sheath microfibers, core-sheath nanofibers, nanoparticles, nanospheres, nanofibers or pure particles of drug. Preferably drug is released from these objects over a period of 7 days. More preferably the drug is released up to 14 days. Drug may be released for up to 30 days or longer. Preferably the kinetic release profile for the drug provides approximately the same dose of drug throughout a given period of time.

In certain embodiments, the invention relates to liquid formulations that are delivered to a body cavity and form foam implants in-situ. The liquid formulation or formulations optionally include an entrained gas or a dissolved gas. In preferred embodiments, the resulting foam implant promotes clotting in a false lumen, or provides a barrier between a true and false lumen, thus preventing profusion of the false lumen. Foam implants of the invention are preferably biocompatible, bioabsorbable, and can be collapsed to be delivered through a low profile delivery device.

In certain embodiments, the invention is a polyurethane foam that is formed in situ in the presence of a initiator (e.g., moisture) from a one-part formulation as previously described. The initiator may be provided by the body or delivery system. The preferred formulation includes an NCO functionalized prepolymer, and optionally includes catalysts, surfactants, crosslinkers, and diluents. The preferred isocyanate compound is a multifunctional aliphatic compound such as isophorone diisocyanate (IPDI) or hexamethylene diisocyanate (HDI). The preferred viscosity is 1 to 3,000 cP, and preferably about 1 to 1,000 cP. Air, carbon dioxide or other auxiliary blowing agents are optionally entrained into either the isocyanate or polyol phases prior to delivery to the patient or, alternatively, are introduced during delivery as a component of the formulation.

In certain embodiments, the invention is a polyurethane foam that is formed in-situ from a two-part formulation as previously described. The first part of the formulation includes an isocyanate compound such as hexamethylene diisocyanate (HDI), toluene diisocyanate (TDI), methylene diphenyl diisocyanate (MDI) or a mixture of MDI isomers, polymeric MDI, isocyanate-functionalized prepolymer, or a polymeric isocyanate having a functionality of preferably between 2.0 and 3.0. The second part of the formulation includes a hydroxyl-functionalized polymer (polyol). The preferred viscosity of the first and second parts of the formulation is 1 to 3,000 cP, and preferably about 2,400 to about 2,600 cP. The polyol phase optionally has multiple polyol species, catalysts, surfactants, chain extenders, crosslinkers, pore openers, fillers, plasticizers and water. Air, carbon dioxide or other auxiliary blowing agents are optionally entrained into either the isocyanate or polyol phases prior to delivery to the patient or, alternatively, are introduced during delivery as a component of the formulation.

The invention will be better understood in the context of certain advantageous characteristics exhibited by foams and formulations of the invention: (i) transport to sites of injury; (ii) lack of interference with bodily functions; (iii) use as a thrombosing agent; and (iv) creation of seals at sites of injury.

Transport to Sites of Injury:

In certain embodiments, foams of the invention reach target sites located within tortuous body cavities, around or across anatomical features, through pooled blood, and/or against the flow of blood. In these embodiments, the formulation can be deposited at a site within a body cavity, which site is optionally either proximal to or remote from a target site that will be treated; the foam will then travel beyond the site of deposition as foaming and expansion is initiated, for example by moving and expanding along a path of least resistance.

The formulation and the foam can be miscible with water, and/or hygroscopic. In certain embodiments, miscibility and hygroscopy are improved by tailoring the pore architecture of the foam to induce capillary action, for example by creating an open-pore architecture within the foam, as is discussed more fully below. In certain preferred embodiments, the mobility of the formulation is facilitated by at least one of the following characteristics: high expansion (1-30× (more preferably 1-10×), or foam density between 1.5-6.3 pounds per cubic foot (pcf)); low viscosity (less than 1,000 cP); foam pore sizes between 10 μm and 10 mm, and hydrophobicity.

Figure 5:
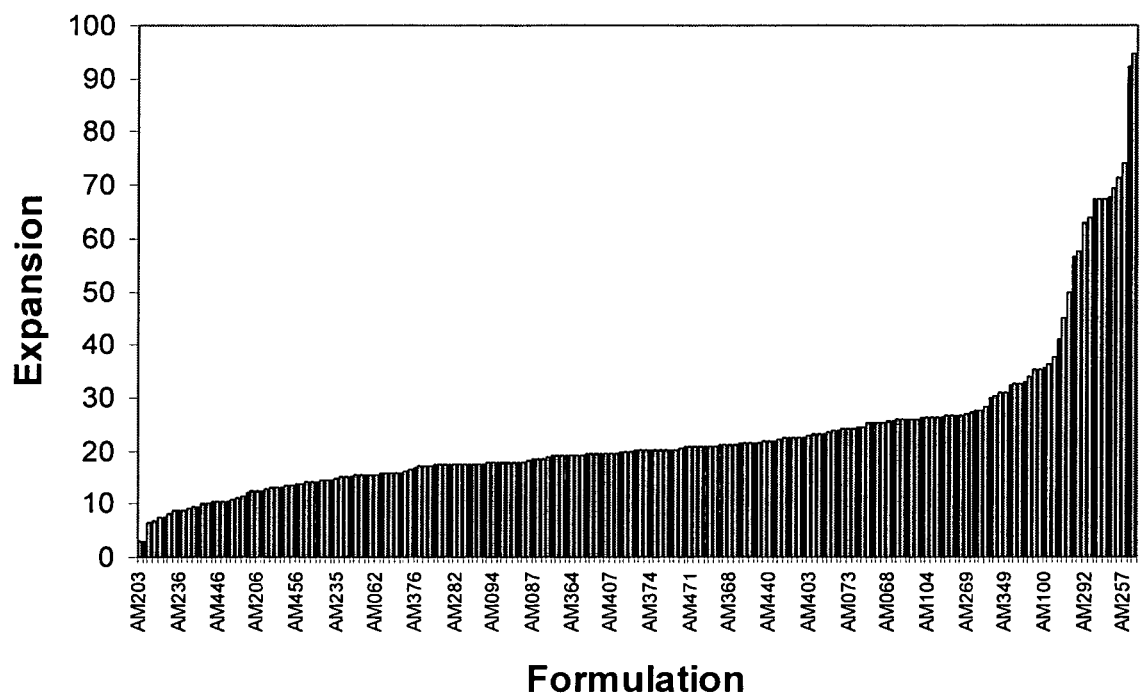
FIG. 5 includes expansion volumes of certain foams of the invention.

With respect to density and expansion, foams have been developed having densities between 10 and 1,000 kg/m$^3$, or having expansions of between 1 and 95 fold, as shown in FIG. 5. In general, increasing the water and/or isocyanate content of the formulation tends to increase the volume expansion. Without wishing to be bound to theory, it is believed that this is due to increased blowing and $CO_2$ evolution. For example, the relatively low 3× expansion of formulation AM203 is increased to 26× in formulation AM201 by increasing the water level of the formulation from 0.45 to 7.2 parts per hundred polyol (pphp). Alternatively, increased expansion can be obtained through the use of blowing catalysts including bis(2-dimethylaminoethyl) ether (DMAEE) and pentamethyldiethylenetriamine (PM-DET), or through the use of catalysts that increase both blowing and gelling including triethylenediamine (TEDA), typically up to 10 pphp. For example, the relatively low 12.5× expansion of formulation AM237 is increased to 57.5× in formulation AM244 by increasing the level of TEDA from 0.4 to 3.2 pphp. It may be preferable to increase stabilization of the polymer when the use of catalysts results in increased expansion. Such increased stabilization can be achieved, for example, by adding surfactants such as Tegostab products (B8629, B9736 LF, 4690, 8871, 8523) and Pluronic products (F-68, F-127); adding more gelling catalysts such as heavy metal catalysts such as stannous octoate and zinc octoate; or with other additives such as solid ammonium bicarbonate. For example, formulation AM251 exhibits 95× expansion and is formulated with high water and catalyst levels and a high isocyanate index.

Figure 6:
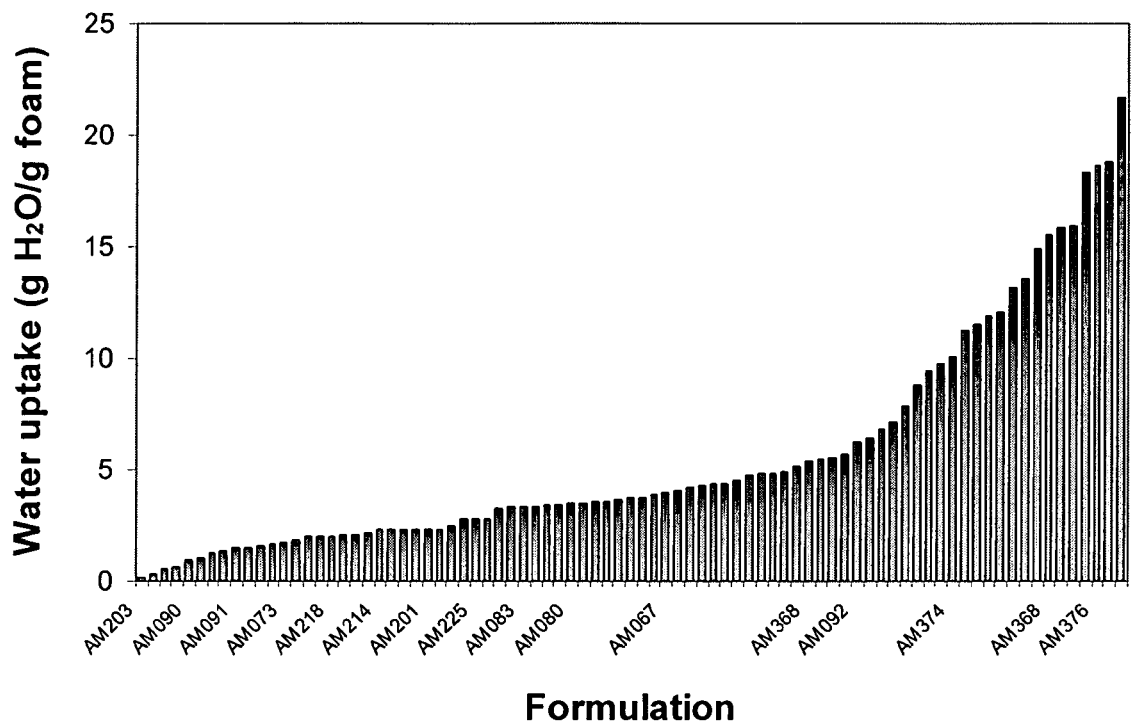
FIG. 6 includes water uptake values of certain foams of the invention.
Figure 7:
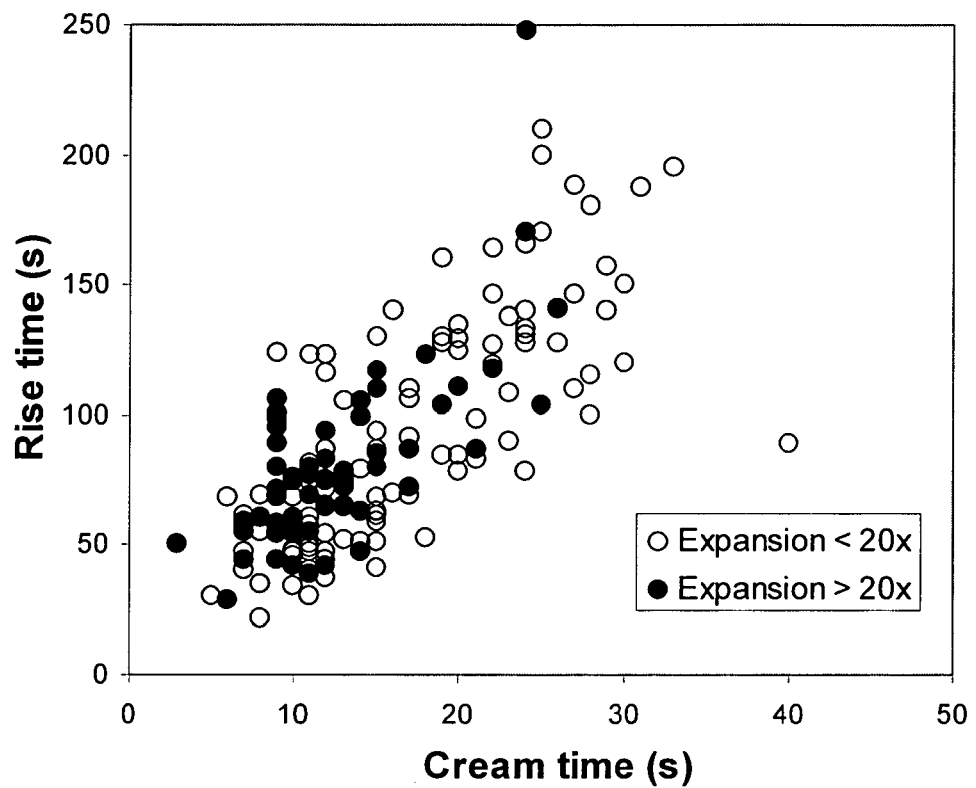
FIG. 7 includes rise time and cream time values for certain formulations of the invention.

With respect to hygroscopy and miscibility with water, the water absorption characteristics of foams can be tailored as well. Foams have been developed having both high and low water absorption, as tested by a 4-minute water immersion test. Results of this test for certain formulations of the invention are depicted in FIG. 6. Water absorption of foams of the invention range between 0 and 22 grams of water absorbed per gram of foam. In certain embodiments, high water uptake is achieved by creating a highly open cell or reticulated foam structure. This architecture is formed by balancing the viscosity of the formulation, the rates of blowing and gelling, the catalyst and surfactant types and levels. Additionally, in certain formulations of the invention, the water content is preferably high (5-10 pphp), the isocyanate index is preferably low (10-50 pphp), and a high-functionality isocyanate is preferably used to provide sufficient crosslinking and rigidity at low concentrations to stabilize the foam and prevent collapse. For example, formulation AM373 has a water uptake of 19.8 grams per gram of foam (g/g). The formulation includes a pore opening ingredient (Ortegol 501), a mixture of three polyols for optimal viscosity (Plurcol, trimethylolpropane ethoxylate, and Poly-G) and crosslinking density, and a high-functionality isocyanate (Lupranate M20). Small changes to the level of Ortegol 501, the amount of water (<0.8 pphp), or the isocyanate index (25-35) in the formulation can dramatically decrease the water uptake characteristics of the foam, even though a reticulated foam architecture may still be formed. Compare, for example, formulation AM368, which has water uptake of 6.4 g/g but which retains the reticulated architecture. Thus, it is believed that foam composition affects water uptake apart from its effects on pore morphology or foam architecture. As another example, formulation AM376 exhibits high water uptake and has a reticulated architecture. The formulation includes a hydrophilic polyol, trimethylolpropane ethoxylate 1014 Da (46 pphp) and has high water uptake (19.7 g/g).

In general, the hydrophilicity of the foam may be improved by increasing the amount of polyethylene glycol (PEG)-based polyols used in the formulation relative to hydrophobic polyols such as those based on polypropylene glycol. Water uptake of foams may also be increased as the PEG-based polyol content is increased, though some rebalancing of catalyst, surfactant, isocyanate and other components may be necessary. Small changes to minor ingredients can significantly improve water uptake. For example, by increasing the surfactant level of formulation 122-009-7 by 2.5-fold, water uptake is increased from 6.7 g/g to 21.7 g/g (compare foam 122-009-10).

Foaming kinetics can be altered by adjusting the types and levels of catalysts and inhibitors used in the formulation. In general, the addition of weak acids such as acetic acid or citric acid delays the start of foaming, but has a limited effect on the rate of foaming once it begins. The rate of foaming can be controlled by adjusting the relative levels of blowing and gelling catalysts. For example, the start of foaming is significantly delayed in formulation AM096 (cream time of 25 seconds, rise time of 105 seconds), but the rate of foaming remains similar relative to formulation AM099 (cream time of 9 seconds, rise time of 95 seconds), yet the two differ only in that the level of acetic acid is 0.5 pphp higher in AM096 than in AM099. Generally, preferred embodiments of the invention maximize cream time and minimize rise time to yield cream times of 15 seconds and higher, and rise times of up to 150 seconds.

The viscosity of formulations of the invention can also be controlled and, without wishing to be bound to any theory, it is believed that lower viscosity of the isocyanate and polyol phases or single prepolymer phase improves dispersion within the body cavity. This could be adventitious if, for example, the material is used to fill the false lumen. Conversely, without wishing to be bound to any theory, it is believed that a higher viscosity of the isocyanate and polyol phases or single prepolymer phase allows the material to remain at the target site. This could be adventitious if, for example, the material is used to seal a tear in the intimal wall and the high viscosity of the material keeps it from traveling away from the tear. Conventionally, polyols used in polyurethane foam formation are multi-functional, OH-terminated polymers with viscosities of between 250 and 5,000 cP. Because high weight percentages are typically used in the art, polyol phases used in foam formulations tend to have similar viscosities. Formulations of the invention, however, may achieve substantially lower phase viscosities by several means, including (i) using higher quantities of water to dilute high-viscosity polyol components; (ii) using low molecular weight (and hence lower viscosity) polyols; and (iii) using non-reactive diluents to the polyol phase. With respect to diluting high-viscosity polyol components with water, a range of water concentrations of 10-20 pphp may be useful for two-part foaming formulations, while in systems using isocyanate prepolymers water levels of 50-100 pphp are preferred. With respect to using low molecular weight polyols, preferred compounds include propylene glycol, di-tri- and tetra-propylene glycols, ethylene glycol, di- tri- and tetra-ethylene glycols, and low molecular weight, linear or multi-armed, hydroxyl-terminated polymers preferably containing 1-10 repeat units such as polypropylene glycols, polyethylene glycols, polytetrahydrofurans, polytetramethylene glycols, and polydimethylsiloxanes. As for non-reactive diluents, between 10-200 pphp of diluent may be added to the polyol phase, and it has been found that a level as high as 300 pphp can be added to some formulations to yield stable foams (e.g. formulation AM1042; 5.6× expansion). Preferred properties for diluents include low viscosity (<50 cP; more preferably 0.5-10 cP), lack of reactivity towards hydroxyls, isocyanates, and other components in the formulation, and biocompatibility. Preferred diluents include propylene carbonate (PC), diethyl malonate, tetraethylene glycol dimethyl ether (TEGDME), and triacetin. A high viscosity can be achieved either by using a high viscosity polymer or prepolymer, or creating a material that crosslinks quickly so that it is low viscosity during delivery but the viscosity increases rapidly upon reaching the target cavity. This rapid viscosity increase can be controlled with catalyst levels and the reactivity of functional groups.

Using low molecular weight polyols and/or diluents, polyol phases have been engineered with viscosities ranging from 17 cP (AM1045) to 2635 cP (AM735). For example, the hydrophobic polyol phase of formulation AM880 (53 cP) combines a low viscosity polypropylene glycol (1200 Da) and the diluents diethyl malonate (15 pphp) with other ingredients. The more hydrophilic polyol phase of formulation AM759 (50 cP) combines trimethylolpropane ethoxylate (1014 Da) with 70 pphp TEGDME and other ingredients. Even with high levels of diluents, foams with high expansion can still be produced (AM1209; 41 cP; 60 pphp TEGDME; 38× expansion) by increasing the catalyst, water, and isocyanate levels.

Figure 8:
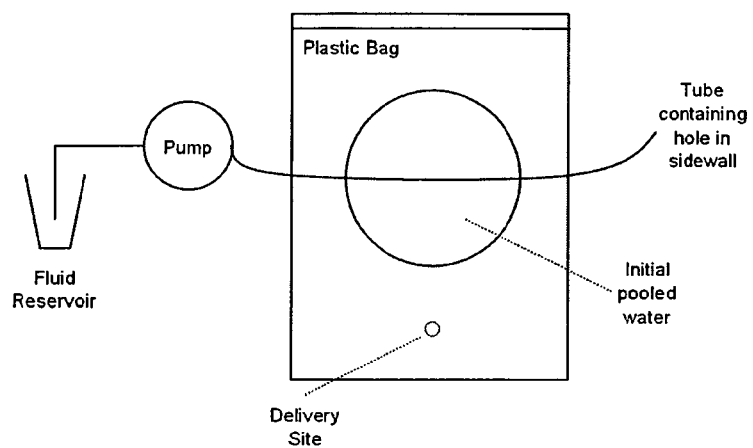
FIG. 8 includes an exemplary schematic illustration of an in-situ apposition assay used to evaluate formulations and foams of the invention.
Figure 9:
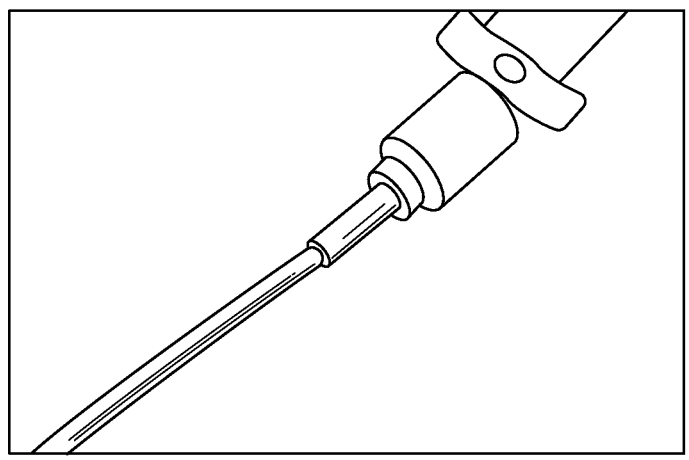
FIG. 9 includes an exemplary photograph of a foam following testing in an in-situ apposition assay.

Using even higher diluent levels (100-300 pphp) enables further reduction of viscosity (e.g., formulation AM1045; 17 cP; 150 pphp PC; 12.1× expansion). In formulations with high levels of diluents, it is noticed that a heterogenous cell structure with large, irregular cells typically forms at the foam base. The addition of ammonium bicarbonate (0.5-20 pphp) can eliminate this heterogeneity. Using ammonium bicarbonate together with high levels of diluents, foams can be generated with >20× expansion (AM1055; 150 pphp PC; 21.8× expansion). Additionally, added diluents may advantageously act as plasticizers and lead to foams with low compression-force at 50% deflection values (CFD), as discussed below (e.g., AM761; 70 pphp TEGDME; 25.8× expansion, 0.3 kPa CFD). An in vitro test to evaluate dispersion and movement of formulations of the invention has been developed, and is shown schematically in FIG. 8. In the test, a tube is placed within a closed container, a plastic bag. A pump is connected to the tube, and a small hole placed in the tube to create a fluid flow orifice. The tube is submerged within a pool of water of known volume. A formulation is tested by delivering it to the plastic bag using a delivery system and, after a selected period elapses, examining the behavior of the formulation by evaluating, among other things, the apposition to the small hole in the tube, the volume of expansion, and the amount of water absorbed during the blowing, gelling, and curing process. A range of formulations have been examined in this in vitro transport test, and a range of outcomes have been observed. Some formulations have advanced and made conformal contact with the flow orifice (e.g., AM096, AM593). In these formulations, the material around the fluid flow did not contain any gaps, tunnels, or flow pathways that indicated poor transport. For example, formulation AM005 was successful in the transport test; the material contacted the flow orifice and was well apposed. The apposition was close enough to create a dimple in the material from the flow orifice, as shown in FIG. 9. Other formulations have not advanced to the flow tube, or have not made conformal contact with the flow orifice (e.g., AM289, AM374, AM244, AM735). Finally, certain formulations displayed an intermediate result, where the flow orifice is partially covered or has a tunnel path of fluid escape through the material (e.g., AM113, AM315, AM746).

A range of formulations have been successful or partially successful in this transport test. Low viscosity, delayed reaction kinetics, and high expansion are all correlated with success in the test. The majority of formulations that have been successful in the test (conformal or near-conformal contact with the flow orifice) have had a viscosity of less than 1200 cP, cream time of more than 10 seconds, and expansion greater than 12×. Finally, hydrophobic formulations have generally performed better in the test than hydrophilic formulations.

Lack of Interference with Bodily Functions:

Foams of the invention are preferably soft and easily compressed so that they do not interfere with physiological functions such as respiration, vasomotion, or cardiac output. For example, in preferred embodiments the foams are sufficiently soft so that, when deployed into the false lumen they do not impinge on the true lumen. In some embodiments, the foams are characterized by CFD values less than 25 kPa to be compressed 50%. Foams having CFD values greater than 25 kPA but less than 60 kPA may be useful in the invention as well.

The foams preferably apply less than 20 mmHg of pressure during long-term use, though the foams may transiently apply pressures in excess of 20 mmHg during the generation and subsequent dissolution of $CO_2$ gas from the isocyanate-water reaction without negative long-term consequences on bodily functions.

Figure 10:
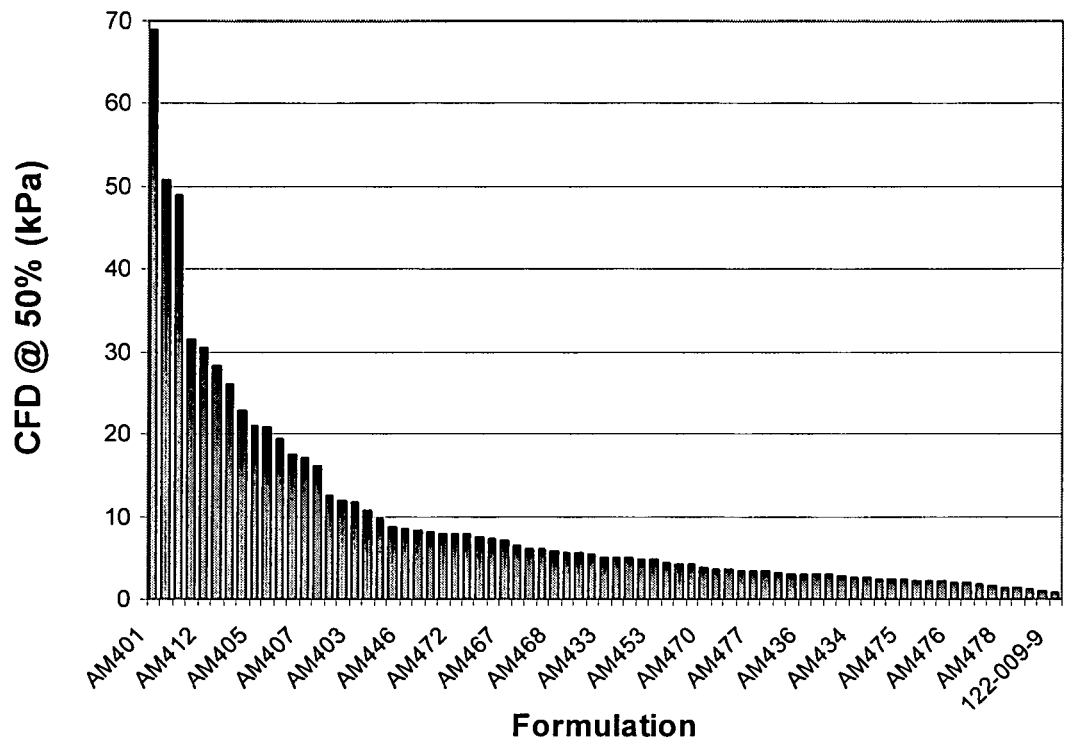
FIG. 10 includes compression force values at 50% compression for certain foams of the invention.

Foams have been developed having CFD values between 0.3 and 100 kPa, as shown in FIG. 10. Soft foams, having low CFD, can be produced using several strategies: (i) using low functionality isocyanates (close to 2.0) so that the crosslink density is minimized, (ii) under-indexing the isocyanate (10-80) so that there is a large excess of polyol and minimal crosslinking, (iii) increasing the polyol molecular weight so that the molecular weight between crosslinks is maximized, (iv) using several polyols to break symmetry and molecular stacking, (v) changing the polyol type to minimize hydrogen bonding and other intramolecular interactions, (vi) increase expansion as outlined above, and (vii) adding plasticizers. An example of a low CFD foam that has been developed is AM376, which takes advantage of drastic isocyanate under-indexing (25) to achieve 0.8 kPa. AM474 is another low CFD foam of interest (2.3 kPa), which is made by moderate under-indexing (70) of a low functionality isocyanate (Mondur MRS-2), in combination with four polyols to break symmetry. In addition, AM761 is an example of a low CFD foam (0.3 kPa) made by under-indexing the isocyanate (31) and adding diluent to plasticize the matrix (70 pphp TEGDME). Without wishing to be bound to any theory, it is believed that modification of the catalyst, surfactant, water, and additive levels can also lead to significant reductions in the CFD. For example, the CFD of 122-001-10 (4.7 kPa) can be reduced over three-fold by changing the surfactant type and levels to produce AM479 (1.3 kPa).

Use as a Thrombosing Agent:

Thrombosis of a false lumen or other structures can restrict blood flow into the false lumen and therefore limit expansion and continued perfusion of the false lumen, which is a preferable condition. Foams of the invention promote thrombosis when injected into a false lumen or other area where thrombosis is desirable. In preferred embodiments foams of the invention contain an agent or agents to induce thrombosis when introduced in a target space in the body. Preferred agents that induce thrombosis include thrombin, chitosan, montmorillonite clays, kaolin, diatomaceous earth, zeolite, cellulose, collagen I-XXIX, gelatin, fibrin, and fibrinogen.

Expanded surface area may also encourage thrombosis by increasing the drag and area at which blot may clot. In preferred embodiments foams of the invention are more porous so as to allow for maximum surface area for the blood to contact, thus inducing clotting. In preferred embodiments, the porosity of the foam is controlled with the surfactant, blowing catalyst, or NCO index.

Although it is desirable to induce thrombosis, it is not always desirable to leave foam permanently in the body. As such, in some embodiments, the foam remains in place long enough for the thrombus to remain stable, but then disintegrates over time. In preferred embodiments, foams of the invention form stably and promote thrombosis of the false lumen, but are biodegradable over time so as not to create a permanent implant. Using a biodegradable polymer soft segment is a preferred method of achieving biodegradable foam, including, for example, polymer soft segments such as polycapralactone, polyglycolide, polylactic acid, or polyanhydrides.

In preferred embodiments, foams of the invention have cell and pore structures with characteristics (including size, morphology, and tortuosity) that permit blood to enter the foam but which provide resistance to blood flow. Without wishing to be bound to theory, hemostasis is thought to be induced by foams of the invention through several mechanisms. First, by reducing blood flow, the foams may assist coagulation and allow stable clots to form. In addition to flow resistance, the foams may provide high polymeric surface area for surface fouling, platelet and cell attachment and activation, and initiation of the coagulation cascade. The preferred properties of the foam to facilitate hemostasis include an open cell structure with pore sizes of 0.01-1 mm, expansion (greater than 1×,), and a high surface-to-volume ratio. Finally, an additional benefit of providing a foam which allows some blood flow into the structure is a reduction of pressure and the exertion of less force in the false lumen as compared to a foam which does not allow some flow.

Figure 11:
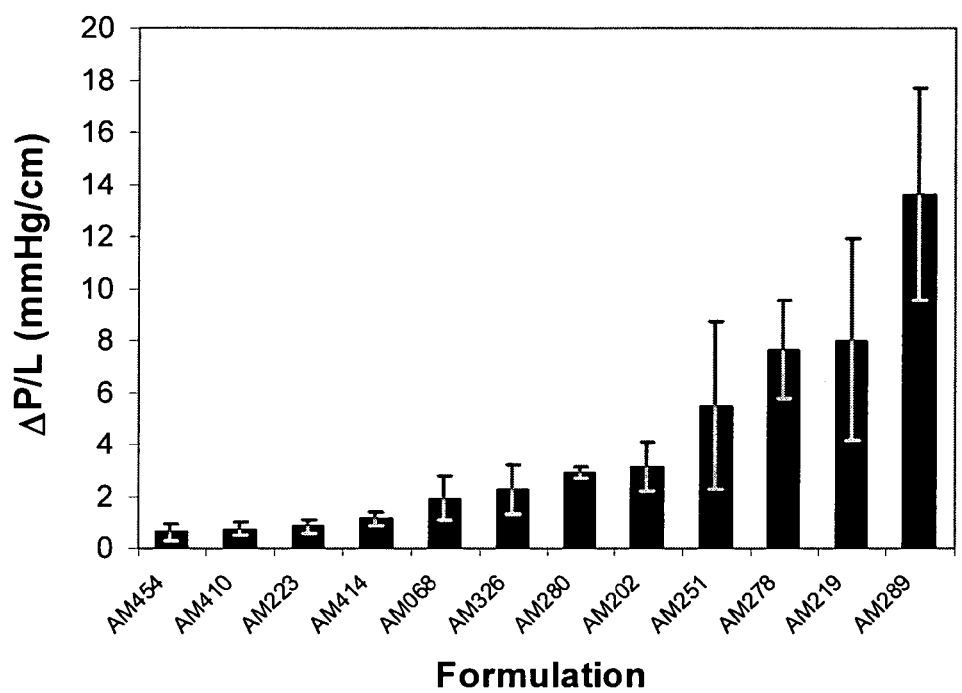
FIG. 11 includes fluid resistivity measurements for certain foams of the invention.

Foams have been developed with high flow resistance, as determined by measuring the pressure drop needed across a length of foam ($\Delta P/L$) to maintain a certain volumetric flow rate, as shown in FIG. 11. While many foam properties can contribute to hydraulic resistance, the combination of pore size and pore density in particular have been shown to affect resistance. For example, formulations AM219 ($\Delta P/L=8.0$ mmHg/cm) and AM289 ($\Delta P/L=13.6$ mmHg/cm) exhibit high flow resistance but have low pore density (11-13 pores/mm$^2$) and small pore size (avg<130 μm). In contrast, formulations AM374 ($\Delta P/L=1.0$ mmHg/cm) and AM376 ($\Delta P/L=1.1$ mmHg/cm) have low flow resistance but have high pore densities (>20 pores/mm2) and large pore sizes (avg>240 μm). However, small pore size and low pore density, alone or in combination, are not necessarily sufficient to achieve high flow resistance. For example, the formulation AM474 has low pore density (8 pores/mm2) but a large pore size (avg~225 μm) and has low flow resistance ($\Delta P/L=1.5$ mmHg/cm). Similarly, formulation AM368 has a small pore size (avg~130 μm) but a relatively high pore density (19 pores/mm2) and low flow resistance ($\Delta P/L=1.7$ mmHg/cm).

Pore density (defined as the number of open pores per unit area) can be controlled by adjusting the types and levels of ingredients in the formulation. In general, pore density can be altered by balancing the isocyanate index, surfactant levels, catalyst levels controlling both blowing and gelling rates, and the polyol viscosity. In many cases, subtle changes to a single ingredient level can drastically change the pore density. For example, it has been found that decreasing the isocyanate index from 45 (in formulation 126-52-4, which has 7 pores/mm2) to 35 (in formulation AM368 which has 19 pores/mm2) while leaving other component concentrations essentially unchanged results in a significantly higher pore density and openness to the structure. In a similar fashion, the pore density of formulation 126-52-2 (12 pores/mm2) can be increased to 19 pores/mm2 (AM368) by only adding 0.37 pphp of the pore opening agent Ortegol 501 to formulation.

Similar to pore density, pore size is affected by a number of ingredient types and levels. For example, the pore size of formulation AM375 (average pore size of approximately 120 μm) can be increased almost three-fold (in AM376; average pore size of approximately 350 μm) by adjusting the relative ratio of Pluracol 816 to TMPEO (17.5:1 to 1:1) while leaving other concentrations essentially unchanged.

Creation of Seals at Sites of Injury:

Foams of the invention may also create a seal when they reach a target site, as discussed above. In certain embodiments, sealing is accomplished by non-specific and non-selective binding of isocyanates in the formulation with exposed tissue surfaces. In other embodiments, sealing can be targeted to certain sites of interest such as exposed basement membranes through targeting means. In certain embodiments, sealing is accomplished by controlling the hydrophobicity of the foam; more hydrophobic materials promote protein adhesion. In still other embodiments, sealing is accomplished by functionalizing the surface with mucoadhesives such as poly vinyl pyrrolidone (PVP), methyl cellulose (MC), carboxymethylcellulose (CMC) or other cellulose derivatives.

In another example of the present invention, a one-part, moisture-cure formulation was deployed into a simple aortic dissection model. The formulation was a custom-synthesized prepolymer with isocyanate functionality, an amidine catalyst, surfactant, diluent, and solid tantalum. A rigid tube was secured to the inside wall of a flexible tube of slightly larger diameter to model the true lumen reinforced by a stent and the aorta, respectively. The space created between the rigid and the flexible tubes represents a false lumen model. The model was submerged in water. The formulation was easily pushed from a syringe through a 7Fr catheter and dispensed along the false lumen, as shown in FIGS. 19A and 19B. The formulation expanded to fill the available space and thereafter cured in about one minute. The foam was viscoelastic, robust and porous, as shown in FIGS. 20A and 20B. As a radiopaque additive, tantalum as incorporated into the formulation to provide visibility during and after formulation delivery and/or foam formation. Other additives such as procoagulents may also be added to the formulation.

In some embodiments, a kit including one or more of the compositions previously discussed (e.g., a kit including a polymer that can be foamed in-situ, a kit including a polymer foam, a device comprising a polymer or polymer foam and any other additive (e.g., external gas, second agent, etc.), a kit comprising a polymer or polymer foam and a delivery system) that can be used to create and/or deploy a polymer foam, or the like, is described. A "kit," as used herein, typically defines a package or an assembly including one or more of the compositions of the invention, and/or other compositions associated with the invention, for example, as previously described. Each of the compositions of the kit may be provided in liquid form (e.g., in solution, as a liquid-phase polymer, etc.), or in solid form (e.g., a reversibly cross-linked polymer). In certain cases, some of the compositions may be constitutable or otherwise processable, for example, by the addition of a suitable solvent, other species, or source of energy (e.g., UV radiation), which may or may not be provided with the kit. Examples of other compositions or components associated with the invention include, but are not limited to, solvents, surfactants, diluents, salts, buffers, emulsifiers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, tapes, adhesives, and the like, for example, for using, administering, modifying, assembling, storing, packaging, preparing, mixing, diluting, and/or preserving the compositions components for a particular use, for example, to a sample and/or a subject.

A kit of the invention may, in certain cases, include different compositions that can be mixed to form a product. In certain embodiments, the kit may include physically separated chambers to hold the compositions, and a mechanism that is activated by a user or a machine for discharging the compositions and/or mixing them together. As a non-limiting example, the kit may include a dual barrel syringe having first and second chambers that contain first and second compositions, wherein the first and second chambers are physically separated, for example by a wall. In this example, the user may depress the plunger of the dual-barrel syringe to eject the first and second compositions from the first and second chambers. In certain embodiments, the kit also includes a static mixing nozzle, a dynamic mixing nozzle, an impeller, or a mixing chamber to permit the components to mix prior to or during discharge. The present invention encompasses both 1-part and 2-part embodiments. In 1-part embodiments, a material is delivered that reacts with bodily fluids to form a foam. In 2-part embodiments, two materials are delivered together that react to form a foam.

A kit of the invention may include a catheter. A delivery catheter to infuse in-situ forming foam may have a small needle. A delivery catheter may have a fanned tip, or have holes along its length. A delivery catheter may contain a balloon or flap to prevent foam expansion. For example, a balloon may be attached on the distal end of the catheter and be inflated to contact the false lumen prior to foam expansion or prior to foam introduction; the inflated balloon then prevents movement into the lumen. A similar effect may be achieved with a flap, cuff, membrane or similar mechanism to contact the false lumen.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the compositions and/or other compositions associated with the kit. In some cases, the instructions may also include instructions for the delivery and/or administration of the compositions, for example, for a particular use, e.g., to a sample and/or a subject, or to deliver the compositions of the invention into contact with bodily tissues to prevent, limit, or otherwise control arterial dissection. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

In the compositions of the invention, the term "alkyl" refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, tert-butyl, cyclobutyl, hexyl, cyclohexyl, and the like.

The term "heteroalkyl" refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, and the like.

The terms "alkenyl" and "alkynyl" refer to unsaturated aliphatic groups analogous in length and possible substitution to the alkyls described above, but that contain at least one double or triple bond respectively.

The terms "heteroalkenyl" and "heteroalkynyl" refer to unsaturated aliphatic groups analogous in length and possible substitution to the heteroalkyls described above, but that contain at least one double or triple bond respectively.

As used herein, the term "halogen" or "halide" designates —F, —Cl, —Br, or —I.

The terms "carboxyl group," "carbonyl group," and "acyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." The term "carboxylate" refers to an anionic carboxyl group. In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

The term "aryl" refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups. In some cases, the The term "alkoxy" refers to the group, —O-alkyl.

The term "aryloxy" refers to the group, —O-aryl.

The term "acyloxy" refers to the group, —O-acyl.

The term "aralkyl" or "arylalkyl", as used herein, refers to an alkyl group substituted with an aryl group.

The terms "heteroaryl" refers to aryl groups comprising at least one heteroatom as a ring atom.

The term "heterocycle" refers to refer to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms. The term "heterocycle" may include heteroaryl groups, saturated heterocycles (e.g., cycloheteroalkyl) groups, or combinations thereof. The heterocycle may be a saturated molecule, or may comprise one or more double bonds. In some case, the heterocycle is a nitrogen heterocycle, wherein at least one ring comprises at least one nitrogen ring atom. The heterocycles may be fused to other rings to form a polycylic heterocycle. The heterocycle may also be fused to a spirocyclic group. In some cases, the heterocycle may be attached to a compound via a nitrogen or a carbon atom in the ring.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine-1,9-diamine, or the like.

The terms "amine" and "amino" are art-recognized and refer to both unsubstituted and substituted amines, e.g., a moiety that can be represented by the 30 general formula: N(R')(R")(R'") wherein R', R", and R'" each independently represent a group permitted by the rules of valence. An example of a substituted amine is benzylamine.

Any of the above groups may be optionally substituted. As used herein, the term "substituted" is contemplated to include all permissible substituents of organic compounds, "permissible" being in the context of the chemical rules of valence known to those of ordinary skill in the art. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein, e.g., a drug or a peptide. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF3, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like. The peptides described herein are inclusive of at least two amino acids connected by amide bond.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

We claim:

1. A method of treating a false lumen adjacent a true lumen within a patient, comprising the steps of:
   covering said false lumen with a balloon;
   injecting a fluid prepolymer material into or onto the false lumen, said prepolymer material comprising a first polyol composition comprising an amine catalyst in an amount up to 10 parts per hundred polyol (pphp), a water content of up to 20 pphp, a surfactant in an amount up to 10 phpp, and a diluent up to 300 pphp mixed with a second composition comprising multiple isocyanate group; and
   forming a foam from said fluid prepolymer material upon injection of said fluid prepolymer material into the false lumen while the balloon is deployed in the true lumen, wherein said foam is formed by a water-triggered reaction of said fluid prepolymer material with water in the body of the patient that results in gas generation and cross-linking and from 1- to 10-fold expansion of the prepolymer material, said gas forcing the material into an interstitial area of said false lumen, said reaction proceeding from the outside-in forming an outer skin on the prepolymer material, said outer skin surrounding the foam and promoting resistance to deformation and movement of the foam into collateral vessels or outside the false lumen, and wherein the deployed balloon acts to contain the foam in the false lumen and resists impingement of the false lumen into the true lumen as the false lumen is filled with the foam.

2. The method of claim 1, wherein said step of injecting said fluid prepolymer material is conducted with a catheter.

3. The method of claim 1, wherein said foam at least partially seals said false lumen.

4. The method of claim 3, wherein said foam substantially seals said false lumen.

5. The method of claim 1, wherein said foam at least partially fills said false lumen.

6. The method of claim 5, wherein said foam substantially fills said false lumen.

7. The method of claim 1, wherein said prepolymer material is injected into a space between said balloon and said false lumen.

8. The method of claim 1, wherein said fluid prepolymer material comprises polyurethane.

9. The method of claim 1, wherein said isocyanate is at least one of hexamethylene diisocyanate, toluene diisocyanate, methylene diphenyl diisocyanate, lysine isocyanate, isophorone diisocyanate, and mixtures thereof.

10. The method of claim 1, wherein said foam is biodegradable.

11. The method of claim 10, wherein said foam comprises a polymer selected from the group consisting of poly(lactic acid), poly(glycolic acid), and polycaprolactone.

12. A method of treating a false lumen adjacent a true lumen within a patient, comprising the steps of:
    covering said false lumen with a medical device;
    injecting a fluid prepolymer material into a space between said medical device and said false lumen, said prepolymer material comprising a first polyol composition comprising an amine catalyst in an amount up to 10 parts per hundred polyol (pphp), a water content of up to 20 pphp, a surfactant in an amount up to 10 pphp, and a diluent up to 300 phpp mixed with a second composition comprising multiple isocyanate groups; and
    forming a foam from said fluid prepolymer material upon injection of said fluid prepolymer material, wherein said foam is formed by a water-triggered reaction of said fluid prepolymer material with water in the body of the patient that results in gas generation and cross-linking and from 1- to 10-fold expansion of the prepolymer material, said gas forcing the material into an interstitial area of said false lumen, said reaction proceeding from the outside-in forming an outer skin on the prepolymer material, said outer skin surrounding the foam and promoting resistance to deformation and movement of the foam into collateral vessels or outside the false lumen, and
    wherein the medical device contains the foam in the false lumen and resists impingement of the false lumen into the true lumen as the false lumen is filled with the foam.

13. The method of claim 12, wherein said foam at least partially seals said false lumen.

14. The method of claim 12, wherein said foam at least partially fills said false lumen.

15. The method of claim 12, wherein said medical device is a graft.

16. A method of treating a false lumen within a patient, comprising the steps of:
    injecting a fluid prepolymer material into the false lumen, said prepolymer material comprising a first polyol composition comprising an amine catalyst in an amount up to 10 parts per hundred polyol (pphp), a water content of up to 20 phpp, a surfactant in an amount up to 10 pphp, and a to 300 pphp mixed a second composition comprising multiple isocyanate group; and
    forming a foam from said fluid prepolymer material upon injection of said fluid prepolymer material, wherein said foam is formed by a water-triggered reaction of said fluid prepolymer material with water in the body of the patient that results in gas generation and cross-linking and from 1- to 10-fold expansion of the prepolymer material, said gas forcing the material into an interstitial area of said false lumen and said reaction proceeding from the outside-in forming an outer skin on the prepolymer material, said outer skin surrounding the foam and promoting resistance to deformation and movement of the foam into collateral vessels or outside the false lumen.

17. The method of claim 16, wherein injection of the fluid prepolymer results in the formation of a coiled structure.

18. The method of claim 16, wherein permeation of water through the outer skin in situ leads to curing of the prepolymer material inside of the outer skin.

19. The method of claim 16, wherein the prepolymer material comprises a reaction product of a diamine and an aliphatic or aromatic diisocyanate.

20. The method of claim 16, wherein the prepolymer material comprises a poly(dimethylsiloxane).

21. The method of claim 16, wherein the foam is a silicone foam.

* * * * *

UNITED STATES PATENT AND TRADEMARK OFFICE
CERTIFICATE OF CORRECTION

PATENT NO. : 10,682,436 B2
APPLICATION NO. : 14/205754
DATED : June 16, 2020
INVENTOR(S) : Toby Freyman et al.

Page 1 of 1

It is certified that error appears in the above-identified patent and that said Letters Patent is hereby corrected as shown below:

In the Claims

In Column 39, Line 38, Claim 1 after "amount up to 10" please remove "phpp" and add --pphp--

In Column 39, Line 40, Claim 1 please remove "group" and add --groups--

In Column 40, Line 24, Claim 12 after "diluent up to 300" please remove "phpp" and add --pphp--

In Column 40, Line 54, Claim 16 after "up to 20" please remove "phpp" and add --pphp--

In Column 40, Line 55, Claim 16 please add --diluent up-- after "and a"

In Column 40, Line 55, Claim 16 please add --with-- after "mixed"

In Column 40, Line 57, Claim 16 please remove "group" and add --groups--

Signed and Sealed this
Tenth Day of November, 2020

Andrei Iancu
*Director of the United States Patent and Trademark Office*